US008062686B2

(12) United States Patent
Gahler et al.

(10) Patent No.: US 8,062,686 B2
(45) Date of Patent: Nov. 22, 2011

(54) DIETARY SUPPLEMENT, AND METHODS OF USE

(75) Inventors: Roland Gahler, Burnaby (CA); Michael Lyon, Nanaimo (CA); Nicole Lee, Coquitlam (CA)

(73) Assignee: InovoBiologics, Inc., Calgary (CA)

( * ) Notice: Subject to any disclaimer, the term of this patent is extended or adjusted under 35 U.S.C. 154(b) by 837 days.

(21) Appl. No.: 11/400,768

(22) Filed: Apr. 7, 2006

(65) Prior Publication Data
US 2006/0228397 A1 Oct. 12, 2006

Related U.S. Application Data

(60) Provisional application No. 60/670,944, filed on Apr. 12, 2005.

(51) Int. Cl.
A23L 1/06 (2006.01)
A23L 1/30 (2006.01)
(52) U.S. Cl. .......... 426/573; 426/96; 426/285; 426/648; 424/489
(58) Field of Classification Search .................... 426/573
See application file for complete search history.

(56) References Cited

U.S. PATENT DOCUMENTS

| | | | |
|---|---|---|---|
| 3,856,945 A | 12/1974 | Sugiyama | |
| 4,676,976 A | 6/1987 | Toba | |
| 4,707,376 A * | 11/1987 | Muraoka et al. | 426/658 |
| 4,734,287 A | 3/1988 | Singer | |
| 4,882,160 A | 11/1989 | Yang | |
| 4,894,250 A | 1/1990 | Musson | |
| 5,049,401 A | 9/1991 | Harada et al. | |
| 5,633,030 A | 5/1997 | Marrs | |
| 6,130,321 A | 10/2000 | Johnson et al. | |
| 6,210,686 B1 | 4/2001 | Bell | |
| 6,511,683 B1 | 1/2003 | Gahler et al. | |
| 6,733,769 B1 | 5/2004 | Ryan | |
| 6,774,111 B1 | 8/2004 | Wolf | |
| 7,067,498 B2 | 6/2006 | Wolf | |
| 7,326,404 B2 | 2/2008 | Vuksan | |
| 2005/0020535 A1 | 1/2005 | Vuksan | |

FOREIGN PATENT DOCUMENTS

| | | |
|---|---|---|
| CA | 2310513 A1 | 11/2001 |
| CA | 2 410 556 A1 | 12/2001 |
| CA | 2604253 A1 | 10/2006 |
| EP | 0 290 251 A1 | 11/1988 |
| GB | 2 349 570 A | 11/2000 |
| JP | 62029947 A | 2/1987 |
| JP | 08301770 A2 | 11/1996 |
| JP | 10028554 A | 2/1998 |
| JP | 2002218945 A | 8/2002 |
| JP | 2002218945 A2 | 8/2002 |
| KR | 2090193 A | 11/2002 |
| KR | 4040890 A | 5/2004 |
| WO | 90/07880 A1 | 7/1990 |
| WO | 95/05939 A1 | 3/1995 |
| WO | 95/06417 A1 | 3/1995 |
| WO | 95/12620 A1 | 5/1995 |
| WO | 99/38393 A2 | 8/1999 |
| WO | 00/18365 A2 | 4/2000 |
| WO | 0067799 A1 | 11/2000 |
| WO | 01/91586 A2 | 12/2001 |
| WO | 2005/092124 A1 | 10/2005 |
| WO | WO 2005/092124 A1 | 10/2005 |

OTHER PUBLICATIONS

Andallu, B., et al., "Effect of Mulberry (*Morus indica* L.) Therapy on Plasma and Erythrocyte Membrane Lipids in Patients With Type 2 Diabetes," *Clinica Chimica Acta* 314:47-53, 2001.
Birketvedt, G.S., et al., "Experiences With Three Different Fiber Supplements in Weight Reduction," *Med. Sci. Monit.* 11(1):15-18, Jan. 1, 2005.
Laifer, S., "New Findings on Fiber," *Life Extension*, May 2005, pp. 34-41.
Ludwig, D.S., et al., "High Glycemic Index Foods, Overeating, and Obesity," *Pediatrics* 103(3):1-6, Mar. 1999.
Marciani, L., et al., "Effect of Meal Viscosity and Nutrients on Satiety, Intragastric Dilution, and Emptying Assessed by MRI," *Am. J. Physiol. Gastrointest. Liver Physiol.* 280:G1227-G1233, 2001.
"Novel Fiber Limits Sugar Absorption," *LE Magazine* (*LifeExtension*), Sep. 2004, pp. 1-19, <http://www.lef.org/magazine/mag2004_all.html> [retrieved Nov. 2, 2006].
Schultes, B., et al., "Modulation of Hunger by Plasma Glucose and Metformin," *J. Clin. Endocrinol. Metab.* 88(3):1133-1141, 2003.
Yip, I., et al., "Liquid Meal Replacements and Glycemic Control in Obese Type 2 Diabetes Patients," *Obesity Research* 9 (Suppl. 4):341S-347S, Nov. 2001.
Ylönen, K., et al., "Associations of Dietary Fiber With Glucose Metabolism in Nondiabetic Relatives of Subjects With Type 2 Diabetes," *Diabetes Care* 26(7):1979-1985, Jul. 2003.
Aro, A., et al., "Improved Diabetic Control and Hypocholesterolaemic Effect Induced by Long-Term Dietary Supplementation with Guar Gum in Type 2 (Insulin-Independent) Diabetes," *Diabetologia* 21:29-33, 1981.
Jenkins, A.L, "Determination of Glycemic Index Lowering Potential of PGX® in Liquid and Solid Food Formulations," unpublished research paper, Glycemic Index Laboratories, Toronto, Canada, Aug. 2, 2006, pp. 1-9.
Jenkins, A.L., et al., "Effect of American Ginseng and Konjac Mannan Fibre on Postprandial Glucose, Insulin, GIP, and GLP-1 Response in Type 2 Diabetes," presented at the Federation of American Societies for Experimental Biology, Washington DC, 2006.
Jenkins, A.L., et al., "Effects of Different Fibres (Non-Starch Polysaccharides) on Bowel Habits in Healthy Individuals," presented at Federation of American Societies for Experimental Biology, Washington DC, 2006.

(Continued)

*Primary Examiner* — Jennifer McNeil
*Assistant Examiner* — Elizabeth Gwartney
(74) *Attorney, Agent, or Firm* — Christensen O'Connor Johnson Kindness PLLC

(57) ABSTRACT

One aspect of the invention provides dietary fiber compositions comprising effective amounts of glucomannan, xanthan gum, and alginate to produce a desired viscosity. The invention also provides food products comprising an effective amount of a dietary fiber composition. In other aspects, the invention provides methods for preparing a dietary fiber composition or a food product comprising a dietary fiber composition, and methods for promoting satiety, promoting weight loss, lowering blood glucose levels, or lowering blood cholesterol levels in a mammal.

27 Claims, 9 Drawing Sheets

OTHER PUBLICATIONS

Jenkins, D.J.A, et al., "Treatment of Diabetes with Guar Gum. Reduction of Urinary Glucose Loss in Diabetics," Lancet 8042:779-780, 1977.

Vuksan, V., et al., "Beneficial Effects of Viscous Dietary Fiber From Konjac-Mannan in Subjects With the Insulin Resistance Syndrome," Diabetes Care, 23(1):9-14, 2000.

Vuksan, V., et al., "Exceptionally Low Blood Glucose Response of Konjac-Mannan (Glucomannan) Fiber Blend Enriched Biscuits in Normal and Diabetic Volunteers," unpublished research paper, University of Toronto, St. Michael's Hospital, and "Dicofarm" Spa, Rome, Italy, Nov. 5, 1989, pp. 1-21.

Vuksan, V., et al., "Konjac-Mannan (Glucomannan) Improved Glycemia and Other Associated Risk Factors for Coronary Heart Disease in Type 2 Diabetes," Diabetes Care, 22(6):913-919, 1999.

Vuksan, V., et al., "The Effect of 2 Particle Sizes of the Viscous Fiber Blend on the Postprandial Glycemic Response Among Healthy Individuals, in Solid and Liquid Meals," unpublished research paper, University of Toronto and St. Michael's Hospital, Apr. 10, 2006, pp. 1-13.

Andallu, B., et al., "Effects of Mulberry (*Morus indica* L) Therapy on Plasma and Erythrocyte Membrane Lipids in Patients With Type 2 Diabetes," Clinica Chimica Acta 314(1-2)0:47-53, Dec. 2001.

Arvill, A., and L. Bodin, "Effect of Short-Term Ingestion of Konjac Glucomannan on Serum Cholesterol in Healthy Men," American Journal of Clinical Nutrition 61(3):585-589, Mar. 1995.

Birketvedt, G.S., et al., "Experiences With Three Different Fiber Supplements in Weight Reduction," Medical Science Monitor 11(1):P15-P18, Jan. 2005.

Blackwood, A.D., et al., "Dietary Fibre, Physicochemical Properties and Their Relationship to Health," Journal of the Royal Society for the Promotion of Health 120(4):242-247, Dec. 2000.

Blundell, J.E., and V.J. Burley, "Satiation, Satiety and the Action of Fibre on Food Intake," International Journal of Obesity 11(Suppl. 1):9-25,1987.

Booth, A.N., et al., "Physiologic Effects of Three Microbial Polysaccharides on Rats," Toxicology and Applied Pharmacology 5:478-484, Jul. 1963.

Bosscher, D., et al., "Effect of Thickening Agents, Based on Soluble Dietary Fiber, on the Availability of Calcium, Iron, and Zinc From Infant Formulas," Nutrition 17(7/8):614-618, Jul. 2001.

Brand, J.C., et al., "Low-Glycemic Index Foods Improve Long-Term Glycemic Control in NIDDM," Diabetes Care 14(2):95-101, Feb. 1991.

Breitman, P.L., et al., "Relationship Between Meal Viscosity and Appetite Control and Food Intake in Adolescents," presented at the CDA/CSEM Canadian Diabetes Association Professional Conference and Annual Meetings, Quebec City, Canada, Oct. 27-30, 2004, 1 page.

Brown, L., et al., "Cholesterol-Lowering Effects of Dietary Fiber: A Meta-Analysis," American Journal of Clinical Nutrition 69(1):30-42, Jan. 1999.

Cameron-Smith, D., et al., "Effect of Soluble Dietary Fibre on the Viscosity of Gastrointestinal Contents and the Acute Glycaemic Response in the Rat," British Journal of Nutrition 71(4):563-571, Apr. 1994.

Chen, H.-L., et al., "Konjac Supplement Alleviated Hypercholesterolemia and Hyperglycemia in Type 2 Diabetic Subjects—A Randomized Double-Blind Tria," Journal of the American College of Nutrition 22(1):36-42, Feb. 2003.

Chiasson, J.-L., et al., "The Effect of Acarbose on Insulin Sensitivity in Subjects With Impaired Glucose Tolerance," Diabetes Care 19(11):1190-1193, Nov. 1996.

Doi, K, et al., "Effect of Glucomannan (Konjac Fiber) on Glucose and Lipid Metabolism in Normal and Diabetic Subjects," in J.S. Melish et al. (eds.), "Genetic Environmental Interaction in Diabetes Mellitus: Proceedings of the Third Symposium on Diabetes Mellitus in Asia and Oceania, Honolulu, Feb. 6-7, 1981," International Congress Series No. 549, Excerpta Medica, Amsterdam, 1982, pp. 306-312.

Doi, K, "Effect of Konjac Fibre (Glucomannan) on Glucose and Lipids," European Journal of Clinical Nutrition 49(Suppl. 3):S190-S197, Oct. 1995.

Doi, K., et al., "Treatment of Diabetes With Glucomannan (Konjac Mannan)," Lancet 1(8123):987-988, May 1979.

Eastwood, M.A., et al., "The Dietary Effects of Xanthan Gum in Man," Food Additives and Contaminants 4(1):17-26, Jan.-Mar. 1987.

Ebihara, K., et al., "Effect of Konjac Mannan, a Water-Soluble Dietary Fiber on Plasma Glucose and Insulin Responses in Young Men Undergone Glucose Tolerance Test," Nutrition Reports International 23(4):577-583, Apr. 1981.

Long, F. and S. Peng, "Effects of Refined Konjac Meal on Zinc, Iron and Calcium Absorption Rates," Yingyang Xuebao [Acta Nutrimenta Sinica] 15(1):73-78, Mar. 1993.

Ferrannini, E., and S. Camastra, "Relationship Between Impaired Glucose Tolerance, Non-Insulin-Dependent Diabetes Mellitus and Obesity," European Journal of Clinical Investigation 28(Suppl. 2):3-7, Sep. 1998.

Frost, G., et al., "Insulin Sensitivity in Women at Risk of Coronary Heart Disease and the Effect of a Low Glycemic Diet," Metabolism 47(10):1245-1251, Oct. 1998.

Howarth, N.C., et al., "Dietary Fiber and Weight Reduction," Nutrition Reviews 59(5):129-139, May 2001.

Huang, C.-Y., et al., "Effect of Konjac Food on Blood Glucose Level in Patients With Diabetes," Biomedical and Environmental Sciences 3(2):123-131, Jun. 1990.

Jenkins, A., et al., "Importance of Administration Mode of Viscous Fibre on Post-Prandial Glycemia," presented at the CDA/CSEM Canadian Diabetes Association Professional Conference and Annual Meetings, Quebec City, Canada, Oct. 27-30, 2004, 2 pages.

Jenkins, A., et al., "Improved Metabolic Control After Long Term Treatment With American Ginseng and Konjac Mannan Fiber in Type 2 Diabetes," presented at the CDA/CSEM Canadian Diabetes Association Professional Conference and Annual Meetings, Ottawa, Oct. 15-18, 2003,1 page.

Jenkins, A., et al., "Reduction in Second Meal Glycemia With Glucomannan Viscous Fibre but Not American Ginseng in Type 2 Diabetes," presented at the CDA/CSEM Canadian Diabetes Association Professional Conference and Annual Meetings, Edmonton, Canada, Oct. 19-22, 2005, 1 page.

Jenkins, A., et al., "Reduction of HbA1c After Long Term Administration of American Ginseng and Konjac Mannan Fiber in Type 2 Diabetes," Diabetes 52(6):A386, Jun. 2003 [Abstract].

Jenkins, D.J.A., et al., "Dietary Fibres, Fibre Analogues, and Glucose Tolerance: Importance of Viscosity," British Medical Journal 1(6124):1392-1394, May 1978.

Jenkins, D.J.A., et al., "Guar Gum in Hyperlipidaemia," Lancet 2(7999):1351, Dec. 1976.

Jenkins, D.J.A., et al., "Implications of Altering the Rate of Carbohydrate Absorption From the Gastrointestinal Tract," Clinical and Investigative Medicine 18(4):296-302, Aug. 1995.

Jenkins, D.J.A., et al., "Viscous and Nonviscous Fibres, Nonabsorbable and Low Glycaemic Index Carbohydrates, Blood Lipids and Coronary Heart Disease," Current Opinion in Lipidology 11(1):49-56, Feb. 2000.

Keithley, J., and B. Swanson, "Glucomannan and Obesity: A Critical Review," Alternative Therapies in Health and Medicine 11(6):30-34, Nov./Dec. 2005.

Kikunaga, S., et al., "The Bioavailability of Magnesium From Wakame (*Undaria pinnatifida*) and Hijiki (*Hijikia fusiforme*) and the Effect of Alginic Acid on Magnesium Utilization of Rats," Plant Foods for Human Nutrition 53(3):265-274, 1999.

Kimura, Y., et al., "Effects of Soluble Sodium Alginate on Cholesterol Excretion and Glucose Tolerance in Rats," Journal of Ethnopharmacology 54(1):47-54, Oct. 1996.

Kodama, T., et al., "Hypocholesterolemic Mechanisms of Non-Nutritive Polysaccharides (Konjac Mannan, Pectin and Carboxymethyl Cellulose) in Foods," Journal of the Japanese Society of Food and Nutrition 25(8):603-608, 1972.

Konishi, F., et al., "Hypertrophic Effect of Unavailable Carbohydrate on Cecum and Colon in Rats," Journal of Nutritional Science and Vitaminology (Tokyo) 30(4):373-379, Aug. 1984.

Krauss, R.M., et al., "AHA Dietary Guidelines: Revision 2000: A Statement for Healthcare Professionals From the Nutrition Committee of the American Heart Association," Circulation 102(18):2284-2299, Oct. 2000.

Laifer, S., "New Findings on Fiber: Research Confirms Benefits of Fiber for Weight Loss, Lower Cholesterol, and Reduced Blood Glucose," Life Extension 11(5):34-41, May 2005.

Loening-Baucke, V., et al., "Fiber (Glucomannan) Is Beneficial in the Treatment of Childhood Constipation," Pediatrics 113(3):e259-e264, Mar. 2004.

Ludwig, D.S., et al., "High Glycemic Index Foods, Overeating, and Obesity," Pediatrics 103(3), Mar. 1999, 6 pages.

Marciani, L., et al., "Effect of Meal Viscosity and Nutrients on Satiety, Intragastric Dilution, and Emptying Assessed by MRI," American Journal of Physiology. Gastrointestinal and Liver Physiology 280(6):G1227-G1233, Jun. 2001.

Marlett, J.A., et al., "Position of the American Dietetic Association: Health Implications of Dietary Fiber," Journal of the American Dietetic Association 102(7):993-1000, Jul. 2002.

Matsuda, M., and R.A. DeFronzo, "Insulin Sensitivity Indices Obtained From Oral Glucose Tolerance Testing," Diabetes Care 22(9):1462-1470, Sep. 1999.

Matsuura, Y., "Degradation of Konjac Glucomannan by Enzymes in Human Feces and Formation of Short-Chain Fatty Acids by Intestinal Anaerobic Bacteria," Journal of Nutritional Science and Vitaminology (Tokyo) 44(3):423-436, Jun. 1998.

Mayer, J., "Regulation of Energy Intake and the Body Weight: The Glucostatic Theory and the Lipostatic Hypothesis," Annals of the New York Academy of Sciences 63(1):15-43, Jul. 1955.

McCarty, M.F., "Glucomannan Minimizes the Postprandial Insulin Surge: A Potential Adjuvant for Hepatothermic Therapy," Medical Hypotheses 58(6):487-490, Jun. 2002.

Morgan, L.M., et al., "The Effect of Soluble- and Insoluble-Fibre Supplementation on Post-Prandial Glucose Tolerance, Insulin, and Gastric Inhibitory Polypeptide Secretion in Healthy Subjects," British Journal of Nutrition 64(1):103-110, Jul. 1990.

Nilson, H.W., and J.A. Wagner, "Feeding Tests With Some Algin Products," Proceedings of the Society for Experimental Biology and Medicine 76(4):630-635, Apr. 1951.

Ohta, A., et al., "The Alginate Reduce the Postprandial Glycaemic Response by Forming a Gel With Dietary Calcium in the Stomach of the Rat," International Journal for Vitamin and Nutrition Research 67(1):55-61, 1997.

Oketani, Y., et al., "Toxicity Studies on Glucomannan (1) Acute Toxicity Study in Mice and Rats," Oyo Yakuri (Applied Pharmacology) 27:127-131, 1984.

Oku, T., et al., "Mechanism of Inhibitory Effect of Unavailable Carbohydrate on Intestinal Calcium Absorption," Journal of Nutrition 112(3):410-415, Mar. 1982.

Osilesi, O., et al., "Use of Xanthan Gum in Dietary Management of Diabetes Mellitus1-3," American Journal of Clinical Nutrition 42(4):597-603, Oct. 1985.

Paradossi, G., et al., "Xanthan and Glucomannan Mixtures: Synergistic Interactions and Gelation," Biomacromolecules 3(3):498-504, May-Jun. 2002.

Pénicaud, L., et al., "Brain Glucose Sensing Mechanism and Glucose Homeostasis," Current Opinion in Clinical Nutrition and Metabolic Care 5(5):539-543, Sep. 2002.

Pittler, M.N., and E. Ernst, "Guar Gum for Body Weight Reduction: Meta-Analysis of Randomized Trials," American Journal of Medicine 110(9):724-730, Jun. 2001.

Renard, E., et al., "Noninsulin-Dependent Diabetes and Glucose Intolerance: Effect of Glucomannan Fibers on Glycemia and Insulinemia," La Semaine des Hôpitaux de Paris 67(6):153-157, Feb. 1991.

Salmerón, J., et al., "Dietary Fiber, Glycemic Load, and Risk of NIDDM in Men," Diabetes Care 20(4):545-550, Apr. 1997.

Salmerón, J., et al., "Dietary Fiber, Glycemic Load, and Risk of Non-Insulin-Dependent Diabetes Mellitus in Women," JAMA 277(6):472-477, Feb. 1997.

Sandberg, A.-S., et al., "Alginate, Small Bowel Sterol Excretion, and Absorption of Nutrients in Ileostomy Subjects," American Journal of Clinical Nutrition 60(5):751-756, Nov. 1994.

Schultes, B., et al., "Modulation of Hunger by Plasma Glucose and Metformin," Journal of Clinical Endocrinology & Metabolism 88(3):1133-1141, Mar. 2003.

Seal, C.J., and J.C. Mathers, "Comparative Gastrointestinal and Plasma Cholesterol Responses of Rats Fed on Cholesterol-Free Diets Supplemented With Guar Gum and Sodium Alginate," British Journal of Nutrition 85(3):317-324, Mar. 2001.

Shatwell, K.P., et al., "Influence of the Acetyl Substituent on the Interaction of Xanthan With Plant Polysaccharides—III. Xanthan-Konjac Mannan Systems," Carbohydrate Polymers 14:131-147, 1991.

Shima, K., et al., "Effect of Dietary Fiber, Konjac Mannan and Guar Gum, on Absorbtion of Sulfonylurea in Man," Nutrition Reports International 26(2):297-302, Aug. 1982.

Stevens, J., et al., "Effect of Psyllium Gum and Wheat Bran on Spontaneous Energy Intake," American Journal of Clinical Nutrition 46(5):812-817, Nov. 1987.

Torsdottir, I., et al., "A Small Dose of Soluble Alginate-Fiber Affects Postprandial Glycemia and Gastric Emptying in Human With Diabetes," Journal of Nutrition 121(6):795-799, Jun. 1991.

Villareal, D.T., et al., "Obesity in Older Adults: Technical Review and Position Statement of the American Society for Nutrition and NAASO, The Obesity Society," American Journal of Clinical Nutrition 82(5):923-934, Nov. 2005.

Viola, S., et al., "Effect of Pectin and Algin Upon Protein Utilization, Digestibility of Nutrients and Energy in Young Rats," Nutrition Report International 1(6):367-375, Jun. 1970.

Vuksan, V., et al., "3-Week Consumption of a Highly Viscous Dietary Fibre Blend Results in Improvements in Insulin Sensitivity and Reductions in Body Fat," presented at the 64th Annual Meeting of the American Diabetes Association, Orlando, Florida, Jun. 4-8, 2004, 2 pages.

Vuksan, V., et al., "Chronic Feeding of Konjac-Mannan (KJM) Fibre Improves Postprandial Glycemia in Insulin Resistance," FASEB Journal 14(4):A727, Mar. 2000 (Abstract 503.7).

Vuksan, V., et al., "Konjac-Mannan and American Ginsing: Emerging Alternative Therapies for Type 2 Diabetes Mellitus," Journal of the American College of Nutrition 20(5):370S-380S, Oct. 2001.

Vuksan, V., et al., "Low Dose of a Highly Viscous Fiber Blend Reduces Postprandial Blood Glucose, Glycemic Index and Increases Satiety in Healthy Individuals," presented at the Natural Health Products Research Society of Canada (NHPRSC) National Research Conference, Montreal, Feb. 20-22, 2004, 1 page.

Walsh, D.E., et al., "Effect of Glucomannan on Obese Patients: A Clinical Study," International Journal of Obesity 8(4):289-293, Jan. 1984.

Williams, J.A., et al., "Inclusion of Guar Gum and Alginate Into a Crispy Bar Improves Postprandial Glycemia in Humans," Journal of Nutrition 134(4):886-889, Apr. 2004.

Wolever, T.M.S., et al., "Beneficial Effect of a Low Glycaemic Index Diet in Type 2 Diabetes," Diabetic Medicine 9(5):451-458, Jun. 1992.

Woodard, G., et al., "Xanthan Gum: Safety Evaluation by Two-Year Feeding Studies in Rats and Dogs and a Three-Generation Reproduction Study in Rats," Toxicology and Applied Pharmacology 24(1):30-36, Jan. 1973.

Wu, J. and S.-S. Peng, "Comparison of Hypolipidemic Effect of Refined Konjac Meal With Several Common Dietary Fibers and Their Mechanisms of Action," Biomedical and Environmental Sciences 10(1):27-37, Mar. 1997.

Yip, I., et al., "Liquid Meal Replacements and Glycemic Control in Obese Type 2 Diabetes Patients," Obesity Research 9(Suppl. 4):341S-347S, Nov. 2001.

Ylönen, K., et al., "Associations of Dietary Fiber With Glucose Metabolism in Nondiabetic Relatives of Subjects With Type 2 Diabetes," Diabetes Care 26(7):1979-1985, Jul. 2003.

Zhang, .M -Y. et al. "The Effect of Foods Containing Refined Konjac Meal on Human Lipid Metabolism," Biomedical and Environmental Sciences 3(1):99-105, Mar. 1990.

Ramsden, L., "Plant and Algal Gums and Mucilages," in P. Tomasik (ed.), Chemical and Functional Properties of Food Saccharides, CRC Press, Boca Raton, Florida, 2004, 5 pages.

Murray, M., "PGX™—New WellBetX™ Approach to Appetite and Blood Sugar Control," Natural Factors Nutritional Products, Dec. 3, 2003, 2-page brochure.

"SlimStyles™ PGX™," Natural Factors Nutritional Products, Jul. 30, 2004, 2-page brochure.

"Slim Styles™: The Revolutionary SlimStyles™ Diet!" Natural Factors Nutritional Products, Apr. 21, 2004, 2-page brochure.

"Superfibre May Be Answer to Battle of the Bulge," CTV.ca, Oct. 29, 2004, <http://www.ctv.ca/servlet/ArticleNews/story/CTVNews/1098979803173_94389003/?hub=Health> [retrieved Nov. 12, 2008], 2 pages.

"Dieters—Say Good-Bye to Unhealthy Diet Fads," SlimStyles with PGX, News Release, Jul. 22, 2004, <http://www.slimstyles.com/articlesJul22-04.htm> [retrieved Nov. 12, 2008], 2 pages.

"Obesity Overburdens Canada's Healthcare System," SlimStyles with PGX, News Release, Jun. 30, 2004, <http://www.slimstyles.com/articlesJun30-04.htm> [retrieved Nov. 12, 2008], 2 pages.

"Solving Syndrome X," Dr. Murray's Natural Facts, Newsletter, Feb. 11, 2004, <http://doctormurray.com/newsletter/2-11-2004.htm> [retrieved Nov. 12, 2008], 4 pages.

"Novel Fiber Limits Sugar Absorption," LE (Life Extension) Magazine, Sep. 2004, 17 pages.

Alvarez-Manceñido, F., et al., "Konjac Glucomannan and Konjac Glucomannan/Xanthan Gum Mixtures as Excipients for Controlled Drug Delivery Systems. Diffusion of Small Drugs," International Journal of Pharmaceutics 349(1-2):11-18, Feb. 2008.

Aoyama, Y., et al., "Effect on Liver and Serum Lipids in Rats of Dietary Additions of Fibers and Cholestyramine to a Cystine-Excess Diet," Agricultural and Biological Chemistry 52(11):2811-2816,1988.

Dea, I.C.M., and E.R. Morris, "Synergistic Xanthan Gels," in P.A. Sandford and A. Laskin (eds.), "ACS Symposium Series," vol. 45, "Extracellular Microbial Polysaccharides," 172nd Meeting of the American Chemical Society, San Francisco, Aug. 30-31,1976, American Chemical Society, Washington, D.C., Jun. 1997, pp. 174-182.

Tako, M., "Binding Sites for Mannose-Specific Interaction Between Xanthan and Galactomannan, and Glucomannan," Colloids and Surfaces B: Biointerfaces 1(2):125-131, Jul. 1993.

Tako, M., "Synergistic Interaction Between Xanthan and Konjac Glucomannan in Aqueous Media," Bioscience, Biotechnology, and Biochemistry 56(8):1188-1192, Aug. 1992.

Tye, R.J., "Konjac Flour: Properties and Applications," Food Technology 45(3):82-92, Mar. 1991.

Venter, C.S., et al., "The Effects of the Dietary Fibre Component Konjac-Glucomannan on Serum Cholesterol Levels of Hypercholesterolaemic Subjects," Human Nutrition: Food Sciences and Nutrition 41F(1):55-61,1987.

Ludwig, D.S., et al., "High Glycemic Index Foods, Overeating, and Obesity," Pediatrics 103(3):e26, Mar. 1999, 6 pages.

Ludwig, D.S., et al., "Dietary Fiber, Weight Gain, and Cardiovascular Disease Risk Factors in Young Adults," JAMA 282(16):1539-1546, Oct. 1999.

Vicenzi, M., et al., "Effectiveness of High Viscosity Glucommanan in Biscuit Form (Dicoman Biscuits) to Induce Delayed Gastric Emptying in Obese Patients," Clinical Dietology 17:423-428, 1990 [with English translation].

* cited by examiner

DIETARY SUPPLEMENT, AND METHODS OF USE

CROSS-REFERENCE TO RELATED APPLICATIONS

This application claims the benefit of U.S. Provisional Patent Application No. 60/670,944, filed on Apr. 12, 2005.

FIELD OF THE INVENTION

The invention relates to dietary fiber compositions, and their use to suppress appetite, promote weight loss, and to lower blood glucose and cholesterol levels.

BACKGROUND

Diabetes and hypoglycemia, a condition that may lead to the development of Type 2 diabetes, have become more and more common. It has been found that such conditions are due to increasing insulin resistance of the cells. Diabetic conditions are traditionally managed with insulin injections and various pharmaceuticals to regulate blood sugars. However, diet and weight-loss plays a major role in correcting many metabolic abnormalities associated with diabetes (Yip et al. (2001) *Obesity Res.* 9:341S-347S). Intake of foods high with high glycemic index is known to lead to overeating and obesity (Ludwig et al. (1999) *Pediatrics* 103(3):E26). Therefore, it is preferable that any agent used in the management of diabetic conditions as well as weight-loss be low in glycemic index. It is most preferable if such agents reduce the glycemic index of foods.

A reduction in carbohydrate intake is also required in successful management of diabetic conditions. Diet counseling is helpful, but diabetics experience more food cravings as they experience more frequent states of hypoglycemia (Strachan et al. (2004) *Physiol. Behav.* 80(5):675-82). Additionally, therapies lowering blood glucose levels in diabetic patients are often associated with the undesirable side effect of body weight gain (Schultes et al. (2003) *J. Clin. Endocrinol. Metabol.* 88(3):1133-41). It has been reported that diets high in soluble fiber may reduce the risk of diabetes through increased insulin sensitivity (Ylonen et al. (2003) *Diabetes Care* 26:1979-85). This may result from the possible role of dietary fiber in blood sugar regulation. It has also been reported that high viscosity meals produce a greater sense of fullness compared to low viscosity meals (Marciani et al. (2001) *Am. J. Physiol. Gastrointest. Liver Physiol.* 280: G1227-33).

Thus, there is a need for dietary fiber compositions that assist in the management of diabetic conditions by lowering blood sugar levels and promoting satiety. The present invention addresses this need and others.

SUMMARY

One aspect of the invention provides dietary fiber compositions. Typically, the dietary fiber compositions comprise effective amounts of glucomannan, xanthan gum, and alginate to produce a desired viscosity. In some embodiments, the dietary fiber composition has a viscosity of at least 2000 centipoise after 15 minutes under gastric conditions. In some embodiments, the dietary fiber composition has a viscosity of at least 10,000 centipoise after 15 minutes under intestinal conditions. Some embodiments of the dietary fiber composition comprise from about 48% to about 90% (w/w) glucomannan, from about 5% to about 20% (w/w) xanthan gum, and from about 5% to about 30% (w/w) alginate.

In some embodiments, the invention provides a dietary fiber composition comprising effective amounts of glucomannan, xanthan gum and alginate to produce an initial viscosity of from about 1 to about 3000 centipoise and at least a three-fold increase in viscosity within 15 minutes after ingestion in a mammalian subject.

In some embodiments, the invention provides food products comprising an effective amount of a dietary fiber composition comprising glucomanhan, xanthan gum, and alginate. Exemplary food products include, but are not limited to, dietary supplements and meal replacements. In some embodiments, the food product comprises from about 2% to about 10% (w/w) of the dietary fiber composition, and the dietary fiber composition comprises from about 48% to about 90% (w/w) glucomannan, from about 5% to about 20% (w/w) xanthan gum, and from about 5% to about 30% (w/w) alginate.

Another aspect of the invention provides a method for preparing a dietary fiber composition. In some embodiments, the methods comprise the step of combining glucomannan, xanthan gum, and alginate to provide a dietary fiber composition comprising effective amounts of glucomannan, xanthan gum, and alginate. In some embodiments, the methods further comprise the step of granulating the dietary fiber composition. The dietary fiber composition prepared according to the methods of the invention may comprise from about 48% to about 90% (w/w) glucomannan, from about 5% to about 20% (w/w) xanthan gum, and from about 5% to about 30% (w/w) alginate. In some embodiments, the methods for preparing a dietary fiber composition comprise the step of granulating the composition.

In another aspect, the present invention provides methods of reducing the initial viscosity of a dietary fiber composition comprising glucomannan, comprising the step of granulating the dietary fiber composition.

In another aspect, the invention provides methods of reducing the initial viscosity of a dietary fiber composition comprising glucomannan and xanthan, comprising the step of adding an effective amount of alginate to the composition.

A further aspect of the invention provides methods for promoting satiety, promoting weight loss, lowering blood glucose levels, or lowering blood cholesterol levels in a mammal. In some embodiments, the methods comprise the step of administering to a mammal an amount of a dietary fiber composition effective to promote satiety, to promote weight loss, to lower blood glucose levels, or to lower blood cholesterol levels in the mammal, wherein the dietary fiber composition comprises glucomannan, xanthan gum, and alginate. The dietary fiber composition administered according to these methods may comprise between about 48% and about 70% (w/w) glucomannan, between about 11% and about 13% (w/w) xanthan gum, and between about 9% and about 17% (w/w) alginate.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
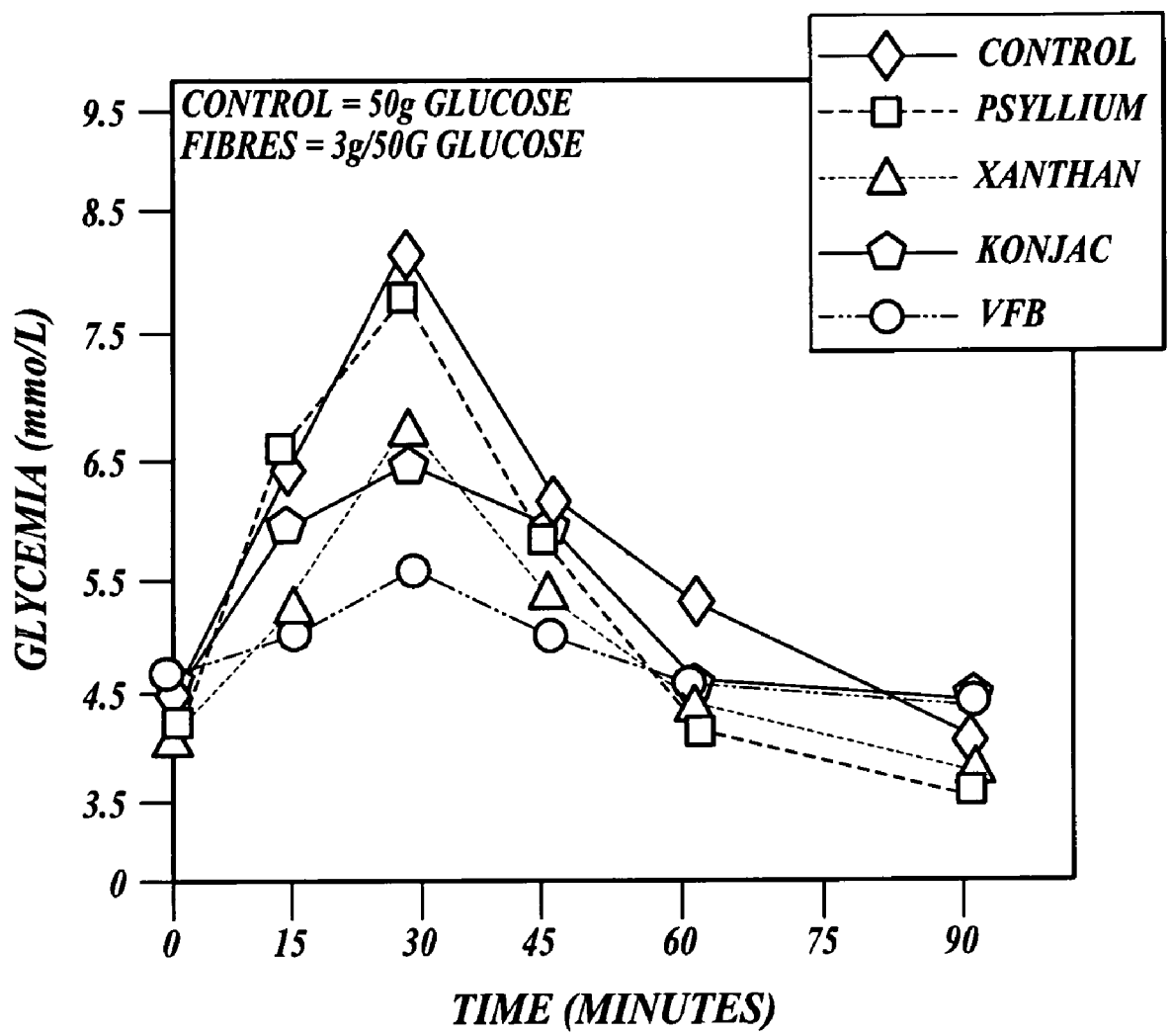
FIG. 1 illustrates the effect of different sources of soluble fibers and viscous fiber blend (VFB) on the glycemic response to a 50 g oral glucose load, as described in EXAMPLE 2.

In one aspect, the invention provides dietary fiber compositions comprising glucomannan, xanthan gum, and alginate. As used herein, "glucomannan" refers to a water-soluble dietary fiber with $\beta$-(1,4)-linked-D-mannose and $\beta$-(1,4)-linked-D-glucose residues in approximately 3:1 ratio and various $\alpha$-linked galactose end groups. It is most commonly isolated from konjac root (*Amorphophallus konjac*) but can also be isolated from other plant sources. "Xanthan gum" refers to an heteropolysaccharide containing glucose, mannose, potassium or sodium glucuronate, acetate, and pyruvate. "Alginate" refers to a mixed polymer of mannuronic and guluronic acid.

The dietary fiber compositions of the invention comprise effective amounts of glucomannan, xanthan gum, and alginate. As used herein, an "effective amount" refers to an amount that produces the desired viscosity. Effective amounts of glucomannan, xanthan gum, and alginate are proportionate amounts of each of these components that produce the desired viscosity when combined. Effective amounts of the dietary fiber composition are amounts of the composition that produce the desired viscosity when ingested. The proportions of glucomannan, xanthan gum, and alginate in the dietary compositions are generally selected to produce a fiber blend that has an initial viscosity that is palatable, but that increases in viscosity substantially over a 15 to 60-minute time period and that maintains or increases in viscosity under gastric or intestinal conditions. As used herein, the term "initial viscosity that is palatable" refers to a range of viscosity from about 1 centipoise to about 3000 centipoise. Liquids with a viscosity of greater than about 3000 centipoise are difficult to ingest and are therefore considered to be non-palatable. As used herein, "initial viscosity" refers to the viscosity of the dietary composition in a 100-fold (w/w) excess of water at a temperature between about 4° C. to about 25° C., for example, between about 16° C. and about 25° C., or equivalent conditions. "Viscosity under gastric conditions" refers to the viscosity of the dietary composition in a 70-fold (w/w) excess of gastric fluid at a temperature between about 16° C. and about 25° C., or equivalent conditions. "Gastric fluid" refers to a solution having a pH of about 1.2 that is made by dissolving 2.0 g of NaCl and 3.2 g of pepsin in 7.0 mL of HCl and sufficient water to make 100 mL (see United States Pharmacopoeia). Gastric conditions may be simulated by adding 10 drops of phosphoric acid to 200 g of distilled water. "Viscosity under intestinal conditions" refers to the viscosity of the dietary composition in a 70-fold (w/w/) excess of simulated intestinal fluid at a temperature between about 16° C. and about 25° C., or equivalent conditions. "Simulated intestinal fluid" refers to a solution having a pH between about 7.5 and about 8.0 that is made as follows: 6.8 g of monobasic potassium phosphate is dissolved in 250 mL of water and mixed. 190 mL of 0.2N NaOH and 400 mL of water is added. This is followed by adding 10.0 g of pancreatin, mixing, adjusting the solution with 0.2N NaOH to a pH of 7.5±0.1, and diluting with water to 1000 mL (see United States Pharmacopoeia).

In some embodiments, the dietary fiber composition has an initial viscosity of between about 1 centipoise (cps) and about 3000 cps (such as from about 200 cps to about 1000 cps or from about 400 cps to about 1000 cps). In some embodiments, the dietary fiber composition has a viscosity under gastric conditions of between about 600 cps and about 5000 cps (such as from about 1000 cps to about 5000 cps or from about 1000 cps to about 3000 cps) after about 30 minutes. In some embodiments, the dietary fiber composition has a viscosity under intestinal conditions of between about 1500 cps and about 8000 cps (such as from about 2000 cps to about 6000 cps or from about 2500 cps to about 6000 cps) after about 30 minutes. In some embodiments, the dietary fiber composition comprises effective amounts of glucomannan, xanthan gum and alginate to produce an initial viscosity of from about 1 to about 3000 centipoise and a least a three-fold increase in viscosity within 15 minutes after ingestion by a mammalian subject, as described in EXAMPLE 1.

The proportions of glucomannan, xanthan gum, and alginate in the dietary fiber compositions may be from about 48% to about 90% of glucomannan (such as from about 60% to about 80%, or from about 60% to about 90%, or from about 65% to about 75%, or from about 50% to about 80%, of from about 50% to about 70%, or about 70%), from about 5% to about 20% of xanthan gum (such as from about 10% to about 20% or from about 11% to about 13%, or from about 13% to about 17%, or about 13%, or about 17%), and from about 5% to about 30% of alginate (such as from about 10% to about 20% or from about 13% to about 17%, or about 13%, or about 17%). In some embodiments, proportions of glucomannan, xanthan gum, and alginate in the dietary compositions are about 70% glucomannan, from about 13% to about 17% xanthan, and from about 13% to about 17% alginate, as described in EXAMPLES 1 and 8.

In some embodiments, the dietary fiber compositions are granulated. As used herein, "granulation" refers to any process of size enlargement in which small particles are gathered together into larger, permanent aggregates. Granulation may be accomplished by agitation in mixing equipment, by compaction, extrusion, or globulation. The dietary fiber compositions may be granulated using various mesh sizes. The term "mesh" refers to the size of the particle as determined by its ability to pass through a screen having holes of defined dimensions. The mesh sizes used herein are Tyler equivalents, as set forth in Table 21-12 of the Chemical Engineers' Handbook (5th ed., Perry & Chilton, eds.) The larger the granulation (i.e., the smaller the mesh size) of the dietary fiber composition, the longer it takes for a desired viscosity to be attained, as shown in EXAMPLE 1. In some embodiments, the dietary fiber composition is granulated using a combined mesh size by separating granulated materials by their particle size, then recombining the particle-size separated granules to give the desired viscosity profile. For example, a combined mesh size of 30 to 60 is obtained by combining granules of 30 mesh (about 600 microns), granules of about 40 mesh (about 400 microns), and granules of about 60 mesh (250 microns).

The dietary fiber compositions of the invention are prepared in a form suitable for oral use according to any method known in the art for the manufacture of oral compositions. For example, the dietary fiber compositions may be prepared as tablets, troches, lozenges, aqueous or oily suspensions, dispersible/dispensable powders or granules (e.g., powders and granules that may be sprinkled on food), emulsions, hard or soft capsules, syrups, elixirs or enteral formulas, or controlled-release compositions. For oral consumption, the dietary compositions may be added to a food or a beverage. For example, a powdered form of the dietary composition may be mixed with an ingestible liquid to form an aqueous beverage or mixed with cookie batter prior to baking. An exemplary formulation of the dietary fiber composition is as hard gelatin capsules, each capsule comprising about 500 mg of the dietary fiber composition.

The dietary fiber compositions of the invention may further comprise additional components. For example, the dietary fiber compositions may additionally comprise magnesium stearate, rice flour, xylitol, lecithin, medium chain triglycerides, flavors, stevia, and/or syloid silica. An exemplary dietary composition comprises about 48% (w/w) glucomannan, about 11% (w/w) xanthan gum, about 9% (w/w) alginate, about 31% (w/w) rice flour, and about 1% (w/w) magnesium stearate. Exemplary dietary fiber compositions are described in EXAMPLES 1, 4, and 5.

In some embodiments, the dietary fiber compositions may include mulberry extract. Mulberry leaf has been shown to possess therapeutic effects on hypoglycemia (see, e.g., *Clin. Chim. Acta* 314 (1-2): 47-53). Therefore, the addition of mulberry extract may enhance the effect of the dietary fiber composition in the regulation of blood sugar levels. However, the addition of mulberry extract dilutes the concentration of the dietary fibers in the compositions, and reduces the viscosity of the overall composition. Therefore, in some embodiments, the dietary fiber compositions of the invention do not include mulberry extract, or contain less than 3.5% of mulberry extract.

The dietary fiber compositions of the invention may be consumed before a meal, during a meal, or after a meal. The dietary fiber compositions of the invention control hunger and induce satiety by providing high viscosity in the gastrointestinal tract. The blend of fibers maintain high viscosities under both the acidic conditions of the stomach and the alkaline conditions in the intestines. The dietary fiber compositions of the invention further assist in the management of diabetic conditions by lowering blood glucose levels.

Another aspect of the invention provides food products comprising an effective amount of a dietary fiber composition comprising glucomannan, xanthan gum, and alginate. The food products of the invention may be dietary supplements or meal replacements. In some embodiments, the food products are provided as shakes or smoothies. Typically, the food products of the invention comprise from about 2% to about 30% (such as from about 2% to about 20%, or from about 5% to about 15%, or from about 2% to about 10%) of a dietary fiber composition comprising glucomannan, xanthan gum, and alginate. Typically, the food products comprise between about 2 grams and about 15 grams of the dietary fiber per serving (such as between about 3 to 8 grams or between about 3 and about 6 grams per serving). In some embodiments, the food products of the invention comprise about 9% (w/w) of a dietary fiber composition comprising glucomannan, xanthan gum, and alginate, as described in EXAMPLES 3 and 7.

The food products of the invention may further contain additional components such as proteins or amino acids, carbohydrates, lipids, vitamins, minerals and co-factors, natural or artificial flavors, dyes or other coloring additives, and preservatives. The term "vitamins" includes, but is not limited to, thiamin, riboflavin, nicotinic acid, panthothenic acid, pyridoxine, biotin, folic acid, vitamin B12, lipoic acid, ascorbic acid, vitamin A, vitamin D, vitamin E, and vitamin K. Also included within the term "vitamins" are cofactors and coenzymes such as coenzymes include thiamine pyrophosphates (TPP), flavin mononucleotide (FMM), flavin adenine dinucleotide (FAD), nicotinamide adenine dinucleotide (AND), nicotinamide adenine dinucleotide phosphate (NADP) Coenzyme A (CoA) pyridoxal phosphate, biocytin, tetrahydrofolic acid, coenzyme B12, lipoyllysine, 11-cis-retinal, and 1,25-dihydroxycholecalciferol. The term "vitamins" also includes choline, carnitine, and alpha, beta, and gamma carotenes. The term "minerals" refers to inorganic substances, metals, and the like required in the human diet, including, but not limited to, calcium, iron, zinc, selenium, copper, iodine, magnesium, phosphorus, chromium, manganese, potassium and the like, and mixtures thereof. The mineral may be in the form of a salt, an oxide, or a chelated salt.

Coloring agents include, but are not limited to, titanium dioxide, and dyes suitable for food such as those known as FD&C dyes and natural coloring agents such as grape skin extract, beet red powder, beta-carotene, annatto, carmine, tumeric, chlorophyll, and paprika. The amount of coloring used may range from about 0.0% to about 3.5% dry weight of the total composition, depending on the saturation of the color.

Flavors incorporated in the composition may be chosen from synthetic flavor oils and flavoring aromatics and/or naturals oils, extracts from plants, leaves, flowers, and fruits, and combinations thereof. These may include, but are not limited to, cinnamon oil, oil of wintergreen, peppermint oils, clove oil, bay oil, anise oil, eucalyptus, thyme oil, cedar leave oil, oil of nutmeg, oil of sage, oils of citrus fruits (including, but not limited to, lemon and orange) oil of bitter almonds and cassia oil. Suitable flavors include, but are not limited to, vanilla, chocolate, mocha, coffee, ice cream, citrus (including lemon, orange, grape, lime, and grapefruit), apple, pear, peach, mango, strawberry, raspberry, cherry, plum, pineapple, and apricot. The amount of flavoring may depend on a number of factors, including the organoleptic effect desired. Flavors may be present in an amount ranging from about 0% to about 10.0% dry weight based upon the dry weight of the composition. Exemplary food products of the invention are provided in EXAMPLES 2, 3, and 7.

In some embodiments, the food products of the invention do not include bilberry extract, lutein, and/or taurine. Some embodiments of the invention provide food products containing less than 28 g of whey protein or less than 8.9 g of fructose. Some embodiments of the invention provide food products containing more than 0.9 g of medium chain triglycerides.

In a further aspect, the invention provides methods for preparing a dietary fiber composition and methods of preparing a food product comprising a dietary fiber composition. In some embodiments, the methods of preparing a dietary fiber composition comprise the step of combining effective amounts of glucomannan, xanthan gum, and alginate to produce an initial viscosity of from about 1 to about 3000 centipoise and at least a three-fold increase in viscosity within 15 minutes after ingestion. In some embodiments, the methods of preparing a dietary fiber composition further comprise the step of granulating the dietary fiber composition.

In some embodiments, the methods of preparing a food product comprising a dietary fiber composition comprise the step of adding an effective amount of a dietary fiber composition comprising glucomannan, xanthan gum, and alginate to a food product. The food products of the invention may be consumed once or several times a day.

In another aspect, the invention provides methods of reducing the initial viscosity of a dietary fiber composition comprising glucomannan. In some embodiments, the method includes the step of granulating the dietary fiber composition comprising glucomannan to produce a composition that has a reduced viscosity. In some embodiments, the dietary fiber further comprises xanthan gum and/or alginate. In some embodiments, the method includes the step of adding an amount of alginate to the composition comprising glucomannan effective to reduce the initial viscosity of the composition, while allowing the composition to increase in viscosity over time, such as after a period of about 120 minutes.

Yet another aspect of the invention provides methods for promoting satiety, promoting weight loss, lowering blood glucose levels, or lowering blood cholesterol levels in a mammal. In some embodiments, the methods comprise administering to a mammal an amount of a dietary fiber composition effective to promote satiety in the mammal, wherein the dietary fiber composition comprises glucomannan, xanthan gum, and alginate. In some embodiments, the methods comprise administering to a mammal an amount of a dietary fiber composition effective to promote weight loss in the mammal, wherein the dietary fiber composition comprises glucomannan, xanthan gum, and alginate. In some embodiments, the methods comprise administering to a mammal an amount of a dietary fiber composition effective to lower blood glucose levels in the mammal, wherein the dietary fiber composition comprises glucomannan, xanthan gum, and alginate. In some embodiments, the methods comprise administering to a mammal an amount of a dietary fiber composition effective to lower blood cholesterol levels in the mammal, wherein the dietary fiber composition comprises glucomannan, xanthan gum, and alginate.

Exemplary dietary fiber composition for use in the methods of the invention are as described above. The dietary fiber compositions may be administered in any form. For example, they may be administered as capsules or they may be administered in a food product.

Exemplary methods of the invention are described in EXAMPLES 2 and 3. As shown in EXAMPLES 2 and 3, the methods of the invention produce significant increases in insulin sensitivity, reduce body fat, and promote satiety and weight loss.

The following examples merely illustrate the best mode now contemplated for practicing the invention, but should not be construed to limit the invention

EXAMPLE 1

This Example describes the selection of fibers in an exemplary dietary fiber composition referred to as a viscous fiber blend (VFB) that provides desirable viscosity profiles under gastric and intestinal conditions.

In formulating VFB, the main objective was to produce a fiber blend that would increase in viscosity substantially over a 30- to 60-minute time period. To enhance palatability, it is desirable for the initial viscosity of the fiber blend to be thinner and for the maximum thickness of the fiber blend to occur in the stomach and intestines of the subject. Therefore, in selecting fibers, the blend also had to maintain or, more desirably, increase in viscosity under both gastric (acidic) and intestinal conditions. The high viscosity at this point in the digestive system would contribute to a feeling of fullness and also help with blood sugar regulation by modulating carbohydrate absorption.

Table 1 shows the viscosity of different fibers tested separately: galactomannan (greater than 80% pure from fenugreek, made by FenuLife), glucomannan (greater than 80% pure from Konjac root), guar gum (commercially sourced galactomannan extract of Cyamopsis tetragonoloba), xanthan gum (commercially sourced extracellular heteropolysaccharide from Xanthomonas bacteria), alginate (commercially sourced medium viscosity sodium alginate from Ascophyllum nodosum, and commercial fiber (consisting of 69% glucomannan, 17% xanthan, 9% carrageenan, and 8% guar, supplied by Dr. Vuksan, and described in U.S. Patent App. No. 20050020535). Two grams of each fiber composition was blended with 200 g of water. Viscosity measurements (in centipoise) were recorded at several time intervals.

TABLE 1

Viscosity Results of Fibers Analyzed Separately

| | Viscosity (centipoise) at Different Time Points(minutes) | | | | | | | | | |
|---|---|---|---|---|---|---|---|---|---|---|
| | 5 | 10 | 15 | 20 | 25 | 30 | 45 | 60 | 75 | 90 | 120 |
| Galactomannan (FenuLife) | 0 | 0 | 50 | 50 | 100 | 200 | 300 | 400 | 450 | 550 | 600 |
| Xanthan | 1400 | 1250 | 1200 | 1300 | 1250 | 1150 | 1150 | 1100 | 1100 | 1100 | 1000 |

TABLE 1-continued

Viscosity Results of Fibers Analyzed Separately

| | Viscosity (centipoise) at Different Time Points(minutes) | | | | | | | | | | |
|---|---|---|---|---|---|---|---|---|---|---|---|
| | 5 | 10 | 15 | 20 | 25 | 30 | 45 | 60 | 75 | 90 | 120 |
| Guar Gum | 2950 | — | 3600 | 3750 | 3800 | 3800 | 3850 | 3850 | 4000 | 3950 | 3950 |
| Glucomannan | 4900 | — | 33000 | 35750 | 38000 | 38750 | 40500 | 43000 | 42500 | 43250 | 44000 |
| Commercial Fiber | 550 | 800 | 1000 | 1100 | 1150 | — | 1350 | 1550 | 1550 | 1750 | 1900 |
| Alginate | 0 | 0 | 0 | 0 | 0 | 0 | 0 | 0 | 0 | 0 | 0 |

Alginate and galactomannan were the least viscous. Xanthan and guar gum reached their maximum thickness almost immediately. Glucomannan displayed a substantial increase in viscosity over time. However, it seemed excessively thick for our purposes, so we analyzed how glucomannan reacted in combination with other less viscous fibers. Viscosity results for combined fiber blends are shown in Table 2.

TABLE 2

Viscosity Results of Fibers Analyzed in Combination

| | Viscosity (centipoise) at Different Time Points(minutes) | | | | | | | | | | |
|---|---|---|---|---|---|---|---|---|---|---|---|
| | 5 | 10 | 15 | 20 | 25 | 30 | 45 | 60 | 75 | 90 | 120 |
| Glucomannan/ Alginate (50:50) | 200 | 400 | 700 | 1100 | 1500 | 2000 | 3050 | 3800 | 4200 | 4700 | 5400 |
| Glucomannan/ Xanthan (50:50) | 1150 | 1300 | 1100 | 1150 | 1150 | 1050 | 1050 | 1100 | 1100 | 1100 | 1100 |
| Glucomannan/ Galactomannan (50:50) | 1050 | — | 2100 | 3900 | 4600 | 4750 | 5400 | 5600 | 5800 | 5850 | 5950 |
| Guar Gum/ Alginate (50:50) | 450 | 700 | 950 | 1100 | 1250 | 1350 | 1550 | 1700 | 1750 | 1820 | 1900 |
| Glucomannan/ Alginate (75:25) | 900 | 2200 | 3900 | — | 4700 | 5450 | 9500 | 14500 | 15600 | 15800 | 16300 |

Alginate, xanthan and galactomannan had a strong thinning affect in combination with glucomannan. Xanthan's property of immediately reaching maximum viscosity carried over when combined with glucomannan. The drawback with this blend is that the initial viscosity was too thick and it did not continue to thicken over time. The alginate and glucomannan blend preserved the characteristic of glucomannan in that it continued to thicken over time. However, the initial viscosity was a bit too watery and it thickened too rapidly. The guar gum and alginate blend did not produce adequate viscosity.

From these results, it was determined that glucomannan was a desirable ingredient for the fiber blend due to its high viscosity property. It also had a very smooth texture which enhanced palatability. Alginate helped moderate the strong thickening characteristic of glucomannan and it also achieved a more palatable viscosity during the initial stages of ingestion. Xanthan, too, was selected as part of the blend since it was the only fiber that seemed to curb and thin out glucomannan near the end of the viscosity test (30-60 minutes). Guar gum and galactomannan did not exhibit any new properties that would contribute to the quality of VFB, therefore they were not selected as part of the fiber blend.

Figure 7:
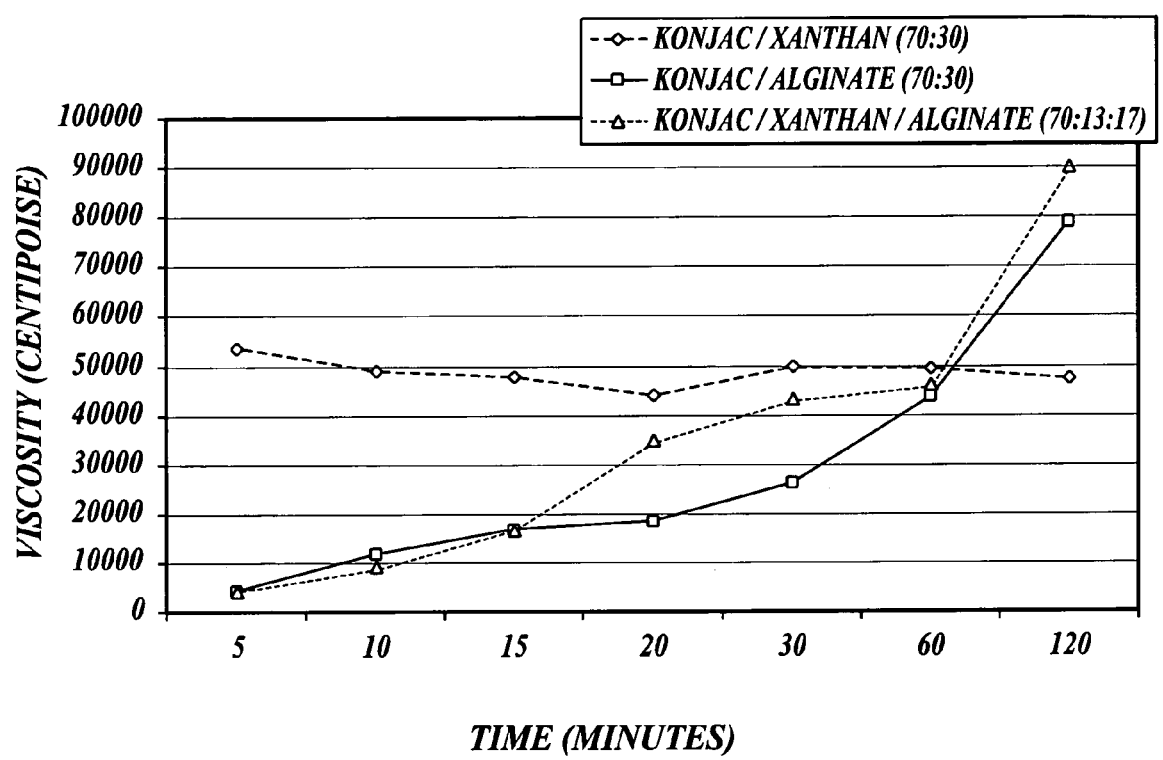
FIG. 7 graphically illustrates the viscosity profile of various fiber blends over time in distilled water, as described in EXAMPLE 8.
Figure 8:
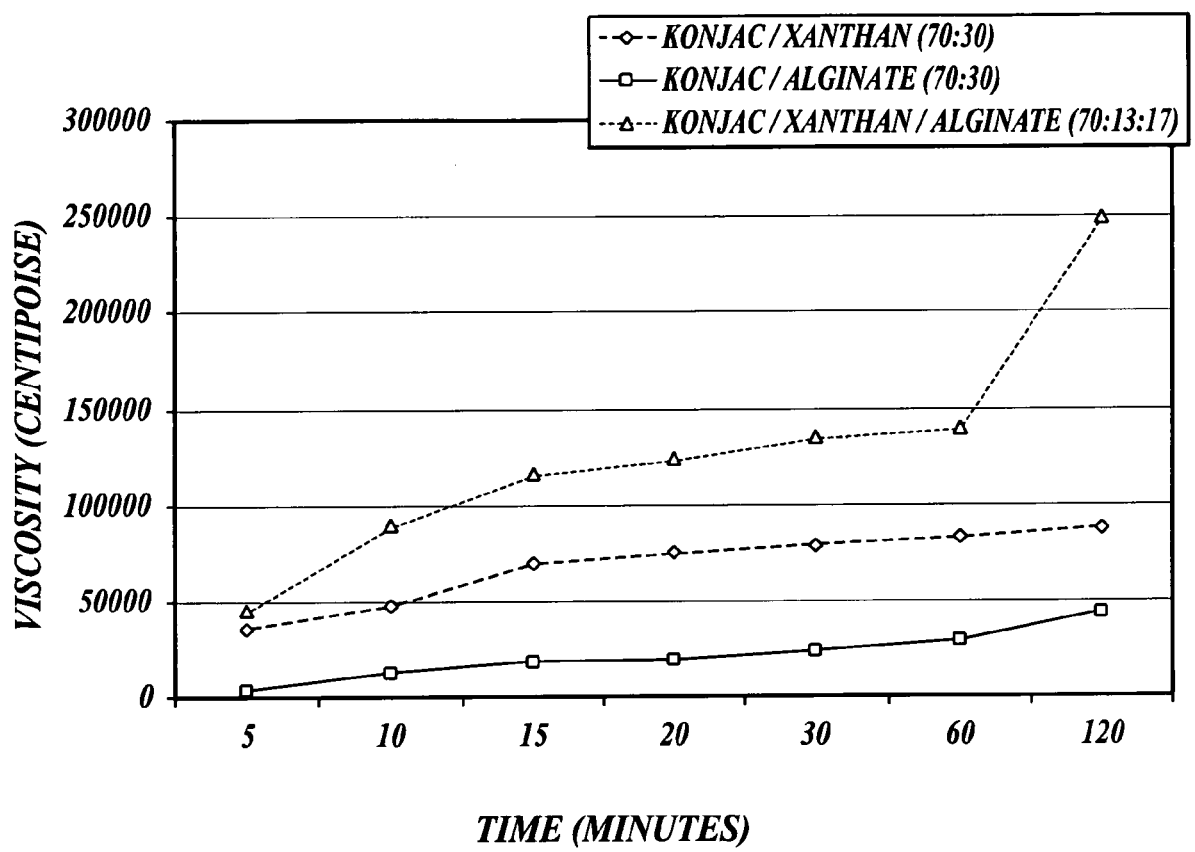
FIG. 8 graphically illustrates the viscosity profile of various fiber blends over time under gastric conditions, as described in EXAMPLE 8.

The final composition of VFB created was from 48%-90% glucomannan, from 5%-20% xanthan gum and from 5%-30% alginate. When glucomannan, xanthan, and alginate are combined at these ratios to produce VFB, this composition exhibits unexpectedly high viscosity values after 120 minutes when blended with water, as shown in FIG. 7, and described in EXAMPLE 8. The VFB also produces unexpectedly high viscosity values after 10 minutes when blended with gastric juice, as shown in FIG. 8, and described in EXAMPLE 8.

At a lower glucomannan ratio, the product would not reach desired thickness. At a higher xanthan ratio, the product also did not reach the desired thickness. At a lower xanthan ratio, the fiber blend thickened too quickly. Alginate also had an important role in enhancing palatability by decreasing viscosity during the initial stages of the product.

In a preferred embodiment, VFB compositions were produced that contained 60%-80% glucomannan, 10%-20% xanthan gum and 10%-20% alginate that had the desirable characteristics mentioned above. For example, a VFB composition was produced that contained 70% glucomannan, 13% xanthan gum and 17% alginate with desirable characteristics as described herein. Another VFB composition was produced that contained 70% glucomannan, 17% xanthan gum and 13% alginate, with similar desirable properties.

The viscosity profile of VFB (70% glucomannan, 13% xanthan gum and 17% alginate) in comparison to a competing commercial fiber is presented in Table 3.

TABLE 3

Viscosity Profile of VFB vs. Commercial Fiber Blend

| | Viscosity (centipoise) at Different Time Points (minutes) | | | | | | | | | |
|---|---|---|---|---|---|---|---|---|---|---|
| | 5 | 10 | 15 | 20 | 25 | 30 | 45 | 60 | 75 | 90 |
| VFB | 600 | 900 | 1000 | 1100 | 1250 | 1300 | 1500 | 1650 | 1750 | 1850 |
| Commercial Fiber | 550 | 800 | 1000 | 1100 | 1150 | | 1350 | 1550 | 1550 | 1750 |

The viscosity profile of VFB (70% glucomannan, 13% xanthan gum and 17% alginate) in comparison to a competing commercial fiber in a smoothie is presented in Table 4. Five grams of fiber were added to a smoothie mix (see EXAMPLE 6 for composition of exemplary smoothie) and 350 g of distilled water was then added.

TABLE 4

Viscosity Profile of VFB vs. Commercial Fiber Blend in Smoothie

| | Viscosity (centipoise) at Different Time Points (minutes) | | | | | | | | |
|---|---|---|---|---|---|---|---|---|---|
| | 5 | 10 | 15 | 20 | 25 | 30 | 45 | 60 | 90 |
| VFB | 2575 | 3525 | 4100 | 4450 | 4815 | 5300 | 6000 | 6700 | 7350 |
| Commercial Fiber | 865 | 1050 | 1140 | 1290 | 1375 | 1400 | 1690 | 1725 | 2050 |

One of the differences between VFB and the commercial fiber is how they react under simulated digestive conditions. As shown in Tables 5 and 6, VFB has the ability to increase in thickness under gastric conditions. Table 5 compares the viscosity profiles of VFB (70% glucomannan, 13% xanthan gum and 17% alginate) and the commercial fiber when 2 grams of fiber is added to 200 g of distilled water with 10 drops of phosphoric acid.

TABLE 5

Viscosity Comparison of VFB and Commercial Fiber under Gastric Conditions

| | Viscosity (centipoise) at Different Time Points (minutes) | | | | | | |
|---|---|---|---|---|---|---|---|
| | 5 | 10 | 15 | 20 | 25 | 30 | 45 |
| VFB | 1000 | 2800 | 4100 | 5100 | 6150 | 6500 | 7150 |
| Commercial Fiber | 400 | 800 | | 2400 | 3500 | 4450 | 6750 |

Table 6 compares the viscosity profiles of VFB (70% glucomannan, 13% xanthan gum and 17% alginate) and the commercial fiber in a smoothie product under gastric conditions. Five grams of Commercial Fiber or 4 g of VFB were added to a smoothie mix (see EXAMPLE 6 for composition of exemplary smoothie) and 350 g of gastric fluid was then added.

TABLE 6

Viscosity Comparison of VFB and Commercial Fiber in Smoothie under Gastric Conditions

| | Viscosity (centipoise) at Different Time Points (minutes) | | | | | | | |
|---|---|---|---|---|---|---|---|---|
| | 5 | 10 | 15 | 20 | 25 | 30 | 45 | 60 |
| VFB | 1500 | 1850 | 2150 | 2450 | 2550 | 2600 | 2950 | 3600 |
| Commercial Fiber | 1550 | 1900 | 1950 | 2200 | 2300 | 2350 | 2700 | 3325 |

Table 7 compares the viscosity profile of VFB (70% glucomannan, 13% xanthan gum and 17% alginate) compared with the commercial fiber under intestinal conditions. 2 g of fiber were added to 200 g of intestinal fluid. Intestinal fluid was made by dissolving 6.8 g of monobasic potassium phosphate in 250 mL of water, mixing, and adding 190 mL of 0.2N NaOH and 400 mL of water. 10.0 g of pancreatin was added, followed by mixing and adjusting the pH with 0.2N NaOH to a pH of 7.5±0.1. The solution was diluted with water to 1000 mL (United States Pharmacopoeia).

TABLE 7

Viscosity Profile Comparison of VFB and Commercial Fiber under Intestinal Conditions

| | Viscosity (centipoise) at Different Time Points (minutes) | | | | | | | | |
|---|---|---|---|---|---|---|---|---|---|
| | 3 | 5 | 10 | 15 | 20 | 25 | 30 | 45 | 60 |
| VFB | 2600 | 6600 | 15000 | 35000 | 39250 | 41000 | 66500 | 69500 | 72000 |
| Commercial Fiber | 1150 | 1350 | 1700 | 2250 | 2600 | 3000 | 3000 | 5850 | 7900 |

Table 8 compares the viscosity profile of VFB (70% glucomannan, 13% xanthan gum and 17% alginate) compared with the commercial fiber under intestinal conditions. Five grams of commercial fiber or 4 g of VFB were added to a smoothie mix (see EXAMPLE 6 for composition of exemplary smoothie) and 350 g of intestinal fluid was then added.

TABLE 8

Viscosity Profile Comparison of VFB and Commercial Fiber in Smoothie under Intestinal Conditions

| | Viscosity (centipoise) at Different Time Points (minutes) | | | | | | | | |
|---|---|---|---|---|---|---|---|---|---|
| | 3 | 5 | 10 | 15 | 20 | 25 | 30 | 45 | 60 |
| VFB | 1250 | 2200 | 4200 | 5250 | | 6800 | 9000 | 15700 | 16600 |
| Commercial Fiber | 1150 | 1300 | 1450 | 1750 | 1900 | 2100 | 2250 | 2350 | 3350 |

These test results show that under simulated gastric and intestinal conditions, the VFB fiber blend thickened more than the commercial fiber blend, indicating that VFB has a higher viscosity than the commercial fibers in the stomach and may continue to thicken under intestinal conditions.

In order to create a product that is more appealing to the consumer, granulated VFB was used to further delay viscosity during the initial stages of ingestion. Granulation is achieved through addition of 30-60% (w/w) water to the VFB blend, and then drying off the added water. This process is typically performed through mechanical granulators, fluid-bed granulator/dryers, mechanical agglomerators, or simple mixing followed by oven or vacuum drying.

Non-granulated VFB is quite fine and tends to clump when added with water. It absorbs moisture so quickly that the water actually encapsulates the powder. However, granulated VFB avoids this problem as the larger granules remain separated from each other when wet. Slowly the slurry thickens as the VFB granules gradually dissolve into water.

Determining the proper mesh size of VFB is important in the granulation process. 30 mesh particles are about 600 microns in diameter, 40 mesh particles are about 400 microns in diameter, 50 mesh particles are about 300 microns in diameter, 60 mesh particles are about 250 microns in diameter, and 80 mesh particles are about 180 microns in diameter. Although it slows viscosity increase, the granulated VFB product still increases to the desirable thickness responsible for generating that full feeling and also regulating blood sugar levels by slowing down absorption of carbohydrates in the intestines. The larger the granulation (i.e., the smaller the mesh size), the more the increase in viscosity is delayed, as shown in Table 9.

TABLE 9

Viscosity Comparison of VFB Granulated Using Different Mesh Sizes

| | Viscosity (centipoise) at Different Time Points (minutes) | | | | | | |
|---|---|---|---|---|---|---|---|
| | 5 | 10 | 15 | 20 | 30 | 60 | 120 |
| Granulated VFB mesh size 30 (stirred) | 0 | 35 | 100 | 195 | 425 | 3760 | 45240 |
| Granulated VFB mesh size 40 (stirred) | 55 | 220 | 490 | 2095 | 6545 | 28780 | >90000 |
| Granulated VFB mesh size 60 (stirred) | 590 | 4295 | 12090 | 28755 | 53035 | 82630 | >90000 |
| Non-granulated VFB (blended) | 612.5 | 1126 | 2356 | 3367.5 | 7880 | 19400 | 48860 |
| Non-granulated VFB (stirred) | 190 | 620 | 5073 | 7150 | 15380 | 56990 | >90000 |
| Granulated VFB combined mesh size 30-60 | 95 | 315 | 1115 | 4330 | 11215 | 48800 | >90000 |

A combination of 30-60 mesh size granulated VFB product consisting of a 1:1:1 combination of 30, 40, and 60 mesh size granules is desirable. A larger proportion of the smaller mesh will delay the increase in viscosity even more.

EXAMPLE 2

This Example describes that consumption of an exemplary dietary fiber composition (VFB) of the invention results in improvements in insulin sensitivity and reductions in body fat.

A 5%-10% loss in body fat can decrease the risk factors associated with the metabolic syndrome (Krauss et al. (2000) *Circulation* 102(18):2284-99). Common weight-loss strategies, such as pharmacological treatments, hypocaloric diets and fad diets do not target appetite, are difficult and costly to maintain, do not address many of the metabolic abnormalities associated with obesity and type 2 diabetes, and result in weight regain and reestablishment of comorbidities once they are discontinued.

Prospective studies demonstrate that high dietary fiber is strongly and inversely related to body weight, satiety, and energy intake (Stevens et al. (1987) *Am. J. Clin. Nutr.* 46(5):

812-7; Blundell & Burley (1987) *Int. J. Obes.* 11 Suppl. 1:9-25; Howarth et al. (2001) *Nutr. Rev.* 59(5):129-39). Evidence also suggests that high soluble fiber intake is associated with improvements in insulin sensitivity and glycemia (Salmeron et al. (1997) *Diabetes Care* 20(4):545-50; Salmeron et al. (1997) *JAMA* 277(6):462-77; Jenkins et al. (1967) *Lancet* 2(7999):1251; Doi et al. (1979) *Lancet* 1(8123):987-8; Shima et al. (1982) *Nutr. Rep. Int.* 26:297-302). Consumption of purified, highly viscous fibers (Brand et al. (1991) *Diabetes Care* 14(2):95-101; Wolever et al. (1992) *Diabet. Med.* 9(5): 451-8) such as guar gum (Jenkins et al. (1977) *Lancet* 2(8042):779-80; Aro et al. (1981) *Diabetologia* 21(1):29-33) and glucomannan (Vuksan et al. (2000) *Diabetes are* 23(1): 9-14) has resulted in improved insulin sensitivity in subjects with insulin resistance, type 2 diabetes, and the metabolic syndrome (Chiasson et al. (1996) *Diabetes Care* 19(11):1190-3; Frost et al. (1998) *Metabolism* 47(10):1245-51).

It is thought that viscous fiber slows digestion and absorption and affects acute and long-term glycemic control and thus leads to appetite control (Meyer (1955) *Ann. NY Acad. Sci.* 63:15-32; Penicaud et al. (2002) *Curr. Opin. Clin. Nutr. Metab. Care* 5(5):539-43) and increased insulin sensitivity. Insulin is known to help regulate fat metabolism and also plays a key role in diabetes. Lowering insulin levels also makes people feel less hungry and this could also explain its link to weight loss.

The present study tested the hypothesis that a metabolically controlled low-fat diet that is supplemented with a blend of highly viscous dietary fibers would improve postprandial glycemic control and insulin secretion as a result of a decrease in body weight and percent body fat. According to the hypothesis, the highly viscous dietary fibers provide mechanical effects (for example, by affecting gastric distension, gastric emptying, gastrointestinal transit time, nutrient absorption rate, and nutrient contact with gastro-intestinal tract), as well as metabolic effects (for example, by affecting hormone secretion, glycemic and insulin responses, short-chain fatty acids, and fecal energy excretion).

Methods

1. Subjects: There were 11 participants in the study. The inclusion criteria are shown in Table 10, the baseline profile of the participants is shown in Table 11.

TABLE 10

Inclusion Criteria

| Risk Factor | Inclusion Criteria |
|---|---|
| Hypertension | Blood Pressure: 135/95 mm Hg = 145 |
| Hyperinsulinemia | Fasting Plasma Insulin: >53 pmol/L |
| Impaired Glucose Tolerance | 2 Hour Post Challenge (Blood) Glucose: 7.8-11.0 mmol/L |
| Overweight | Body Mass Index: <30 kg/m$^2$ |
| Dyslipidemia | High Density Lipoprotein: Men <0.9 mml/l, women <1.2 mm/l |
| | Triglycerides: 2.3-4.5 mmol/l |
| Other | Absence of coronary heart disease, visceral obesity, not taking medications for hyperglycemia, hyperlipidemia or hypertension, less than 2 alcoholic drinks/day, non-smokers |

TABLE 11

Participant Profile

| Parameter | Baseline Profile |
|---|---|
| Fasting Plasma Insulin | 98 ± 13 pmol/l |
| 2-Hour Postprandial Plasma Insulin | 439 ± 68 pmol/l |
| Serum Cholesterol | 5.2-6.7 mmol/l |
| Exercise | Sedentary |
| Mean Age | 55 ± 4 years (range: 46-61) |
| Body Mass Index | 28 ± 1.5 kg/m$^2$ |
| Waist to Hip Ratio | Men: 0.98 ± 0.2 (waist: 96 ± 12 cm) |
| | Women: 0.91 ± 0.4 |
| | (waist: 87 ± 19 cm) |

2. Design: Randomized, double blinded, placebo-control, crossover design. During the 6-week run-in period, participants consumed the National Cholesterol Education Program Therapeutic Lifestyle Changes (TLC) diet. The experimental phase of the study consisted of two successive 3-week treatment periods, separated by a 2-week washout period (with the TLC diet). During the first treatment period, subjects were randomly assigned to either a TLC diet with the viscous fiber blend (VFB) or wheat bran (WB) alone control. For the second treatment period, participants were crossed over. At week 0 and week 3, participants came to the clinic and consumed a test or control breakfast, and postprandial glucose and insulin was assessed along with body weight and % body fat. At the beginning and end of each experimental period, participants were tested for glucose and insulin concentrations at 0, 30, 45, 60, 90, 120, and 180 minutes after a test or control breakfast. Insulin sensitivity was calculated as previously described (Matsuda & DeFronzo (1999) *Diabetes Care* 22:1462-70). Body fat was determined by infra-red interactance (Futrex-5000) at week-0 and week-3.

3. Test Breakfasts: In a crossover design, participants with reduced insulin sensitivity and the metabolic syndrome were assigned to consume a metabolically controlled diet enriched with either 0.5 g/100 kcal of highly viscous dietary fiber (VFB, test breakfast) or matched wheat bran control (control breakfast) over two 3-week periods, separated by a 2-week washout period. The control breakfast consisted of 49 g of wheat bran Cookies, 52 g of bran flakes, 250 mL of 2% milk, and 8 g of butter. The test breakfast consisted of 58 g VFB cookies (containing approximately 10% VFB fibers, 25% sucrose, with a nutrient profile of about 6% protein, 14% fat, 60% available carbohydrates, 1.5% ash, and 2.8% moisture), 69 g bran flakes, 250 mL 2% milk, and 8 g of butter. The two breakfasts were isocaloric and identical in appearance and taste. The nutrient profile of the two breakfasts differed only in the type of fiber, as shown in Table 12.

TABLE 12

Nutrient Profile of Control and Test Breakfast

| | Control Breakfast | Test Breakfast |
|---|---|---|
| Energy | 673 Kcal | 678 Kcal |
| Protein | 10.3% | 11.2% |
| Total Fat | 29.0% | 28.6% |
| Available Carbohydrate | 61.1% | 59.2% |
| Total Fiber | 12.0 g | 11.4 g |
| Soluble Fiber | 1.2 g | 5.4 g |

Results

1. Rheology: Table 13 shows the viscosity of 5 different viscous soluble fiber sources compared to viscous fiber blend (VFB). Measurements of the samples were taken by a Brookfield viscometer (Middleboro, Mass.) on a 1% solution at 24 hour using an "F" spindle at a shear rate of 30 per second. Data are the mean of 3 or more repetitions (cps=centipoises).

TABLE 13

Viscosity Comparison of Different Soluble Fiber Sources

| Soluble Fiber Source | Viscosity (centipoise) |
|---|---|
| Kappa C. | 2000 |
| Phyllium | 6000 |
| Xanthan | 12,000 |
| Guar | 17,000 |
| Konjac 98% | 41,000 |
| VFB | 112,000 |

2. Glycemic Response: FIG. 1 and Table 14 show the effects of administering 3 g of various sources of soluble fibers and VFB administered on the glycemic response to a 50 g oral glucose load. The control is a 50 g oral glucose load alone.

TABLE 14

Effects of Different Soluble Fiber Sources on Area Under the Curve Glucose Response

| Soluble Fiber Source | Under the Curve Glucose Response (mmol/L) |
|---|---|
| Control | 113 |
| Phyllium | 100 |
| Xanthan | 81 |
| Konjac 98% | 80 |
| VFB | 39 |

Figure 2A:
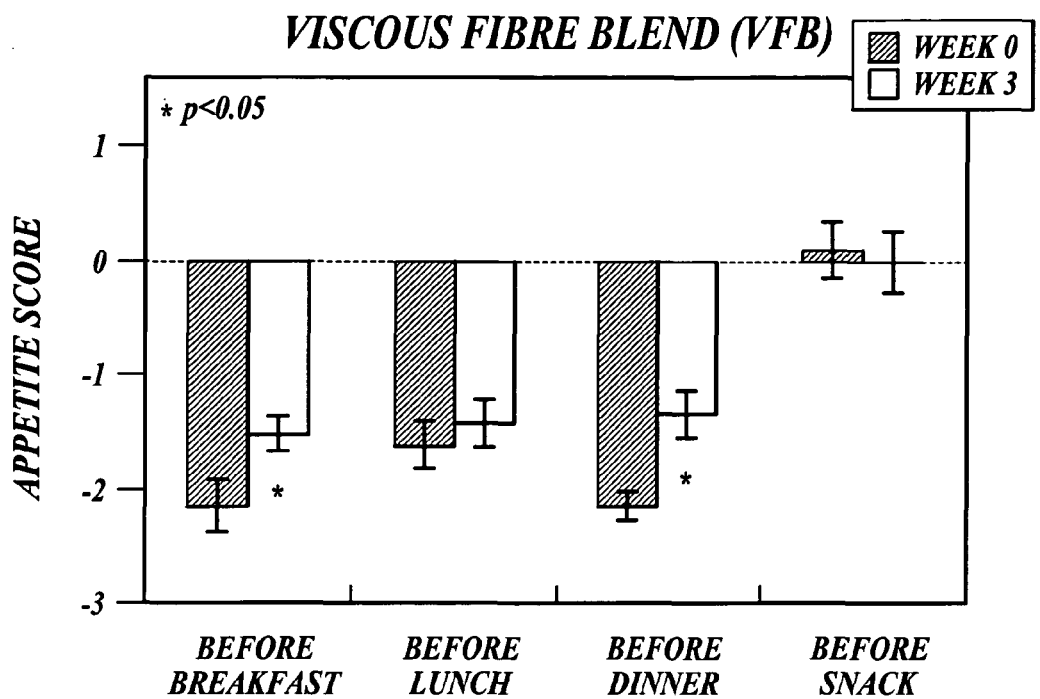
FIG. 2A provides a comparison of subjective appetite ratings before each meal and bedtime snack at week 0 and week 3 in subjects provided with test breakfasts containing VFB cookies, as described in EXAMPLE 2. Data are expressed as means±SD. Significant differences at p<0.05 are indicated by an asterisk.
Figure 2B:
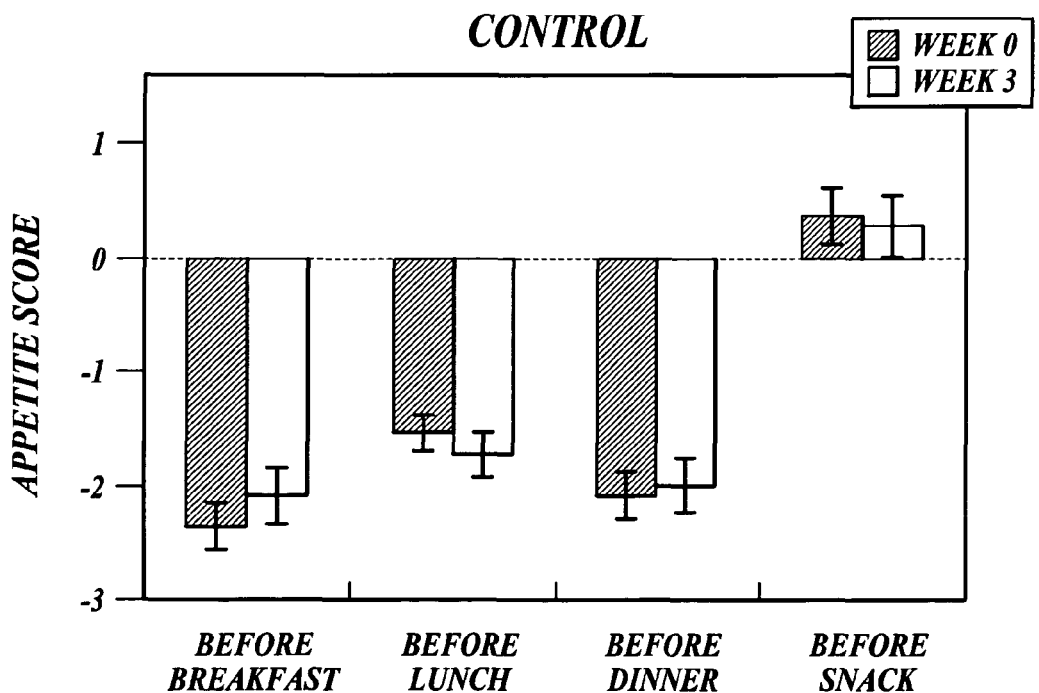
FIG. 2B provides a comparison of subjective appetite ratings before each meal and bedtime snack at week 0 and week 3 in subjects provided with control breakfasts, as described in EXAMPLE 2. Data are expressed as means±SD. Significant differences at p<0.05 are indicated by an asterisk.

3. Appetite Control: FIGS. 2A-B and Table 15 show a comparison of subjective appetite ratings before each meal and bedtime snack at week 0 and week 3 in subjects provided with test breakfasts with VFB (FIG. 2A) and control breakfasts (FIG. 2B). Data are expressed as means±SD. Significant differences at p<0.05 are indicated by an asterisk.

TABLE 15

Comparison of Appetite Ratings in Subjects Provided With Test Breakfasts and Control Breakfasts

| | Appetite Score | | | | | | | |
|---|---|---|---|---|---|---|---|---|
| | Before Breakfast | | Before Lunch | | Before Dinner | | Before Snack | |
| | Week 0 | Week 3 | Week 0 | Week 3 | Week 0 | Week 3 | Week 0 | Week 3 |
| | VFB Treatment | | | | | | | |
| MEAN | −2.18 | −1.55 | −1.64 | −1.45 | −2.18 | −1.36 | 0.09 | 0.00 |
| SEM | 0.23 | 0.16 | 0.20 | 0.21 | 0.12 | 0.20 | 0.25 | 0.27 |
| | Control | | | | | | | |
| MEAN | −2.36 | −2.09 | −1.55 | −1.73 | −2.09 | −2.00 | 0.36 | 0.27 |
| SEM | 0.20 | 0.25 | 0.16 | 0.19 | 0.21 | 0.23 | 0.24 | 0.27 |

Figure 3A:
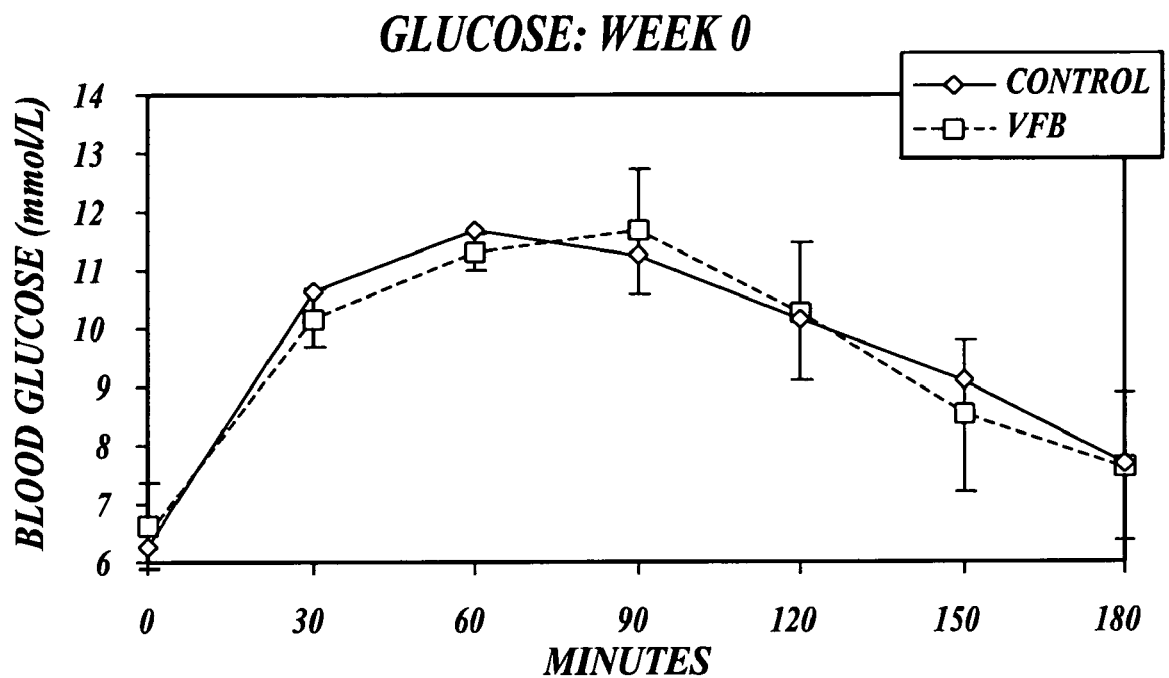
FIG. 3A graphically illustrates the acute postprandial glucose response in subjects provided with control and test breakfasts as measured at the beginning of the study, as described in EXAMPLE 2.
Figure 3B:
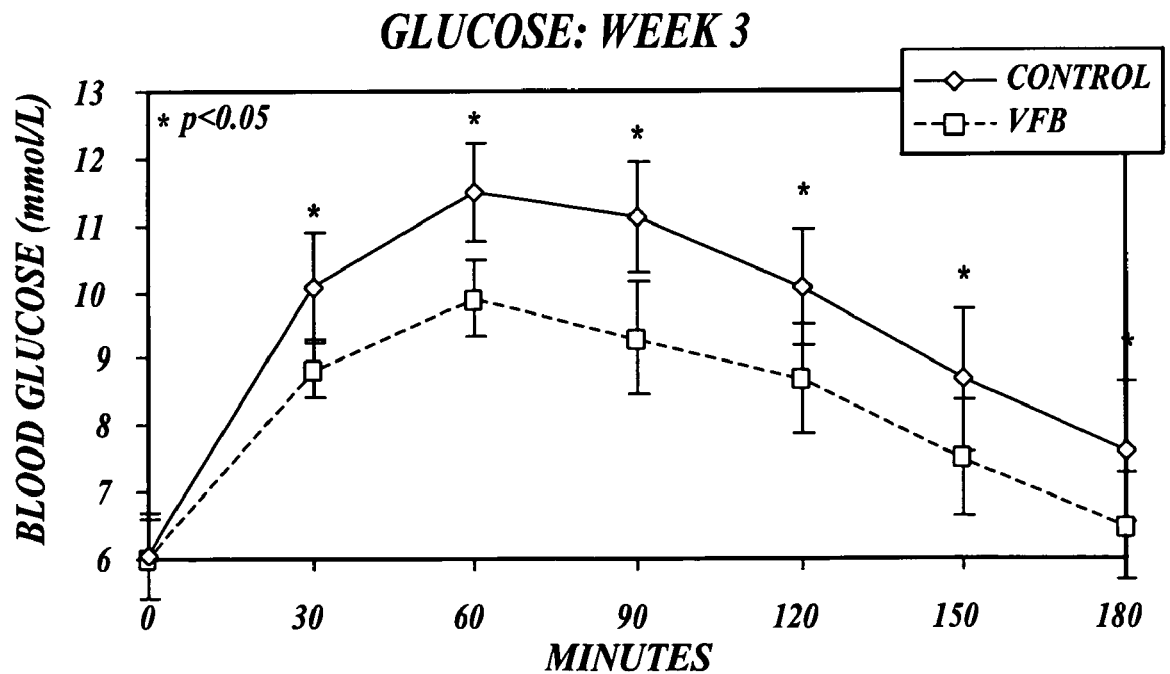
FIG. 3B graphically illustrates the acute postprandial glucose response in subjects provided with control and test breakfasts as measured during the third week of the study, as described in EXAMPLE 2.

4. Glucose: FIGS. 3A-B and Table 16 show a comparison of the acute postprandial glucose response in subjects provided with control and test VFB breakfasts. Subjects were given either the control breakfast or the test breakfast everyday for three weeks. Their blood glucose response was measured at the beginning of the study (week 0) and at the end of the study (week 3). All data points are means±SD. Significant differences at p<0.05 are indicated by an asterisk.

Figure 4:
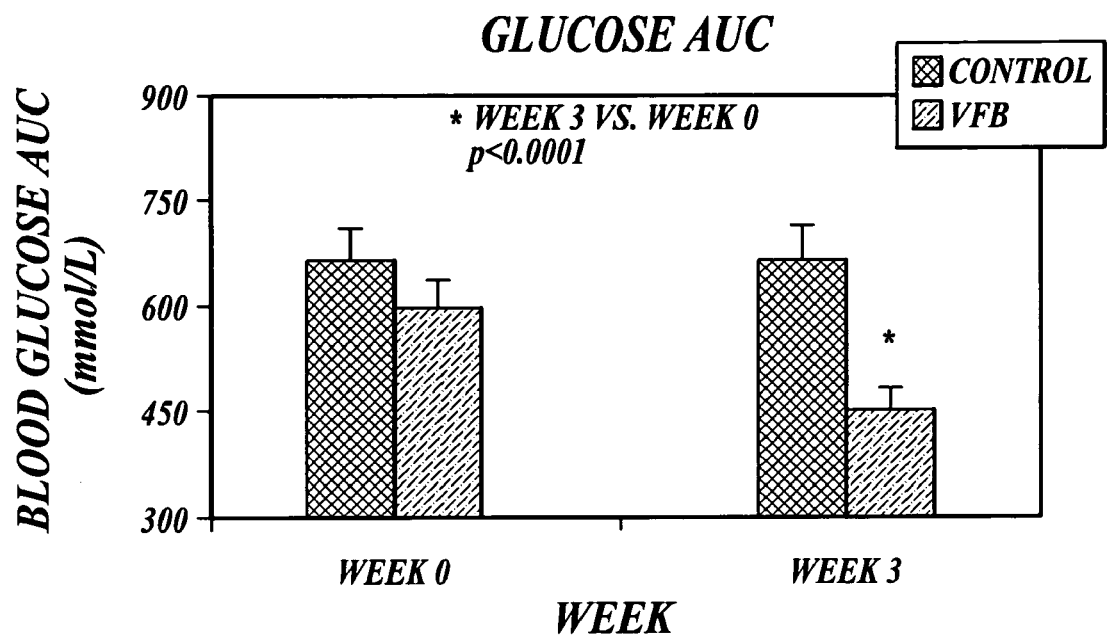
FIG. 4 shows the area under the curves for postprandial glucose responses at week 0 and week 3 for control and VFB, as described in EXAMPLE 2. All data points are means±SD. Significant differences at p<0.05 are indicated by an asterisk.

FIG. 4 shows the area under the curve (AUC) for postprandial glucose response at week 0 and week 3 for control and VFB. All data points are means±SD. Significant differences at p<0.05 are indicated by an asterisk.

TABLE 16

Comparison of Blood Glucose Levels in Subjects Provided with Control and Test Breakfasts

| | Blood Glucose (mmol/L) | | | | | | | |
|---|---|---|---|---|---|---|---|---|
| | 0 min | 30 min | 60 min | 90 min | 120 min | 150 min | 180 min | AUC |
| | Week 0: Control | | | | | | | |
| MEAN | 6.28 | 10.63 | 11.66 | 11.26 | 10.18 | 9.09 | 7.67 | 663.75 |
| SEM | 0.56 | 0.65 | 0.61 | 0.77 | 0.90 | 1.01 | 0.97 | 45.01 |
| | Week 0: VFB Treatment | | | | | | | |
| MEAN | 6.62 | 10.17 | 11.30 | 11.66 | 10.28 | 8.50 | 7.62 | 594.48 |
| SEM | 0.75 | 0.49 | 0.32 | 1.07 | 1.20 | 1.27 | 1.26 | 39.22 |
| | Week 3: Control | | | | | | | |
| MEAN | 6.03 | 10.06 | 11.48 | 11.14 | 10.08 | 8.69 | 7.61 | 666.39 |
| SEM | 0.64 | 0.83 | 0.72 | 0.83 | 0.87 | 1.07 | 1.07 | 46.13 |
| | Week 3: VFB Treatment | | | | | | | |
| MEAN | 6.01 | 8.86 | 9.91 | 9.30 | 8.71 | 7.51 | 6.46 | 451.38 |
| SEM | 0.59 | 0.42 | 0.56 | 0.85 | 0.83 | 0.86 | 0.80 | 28.28 |

Figure 3C:
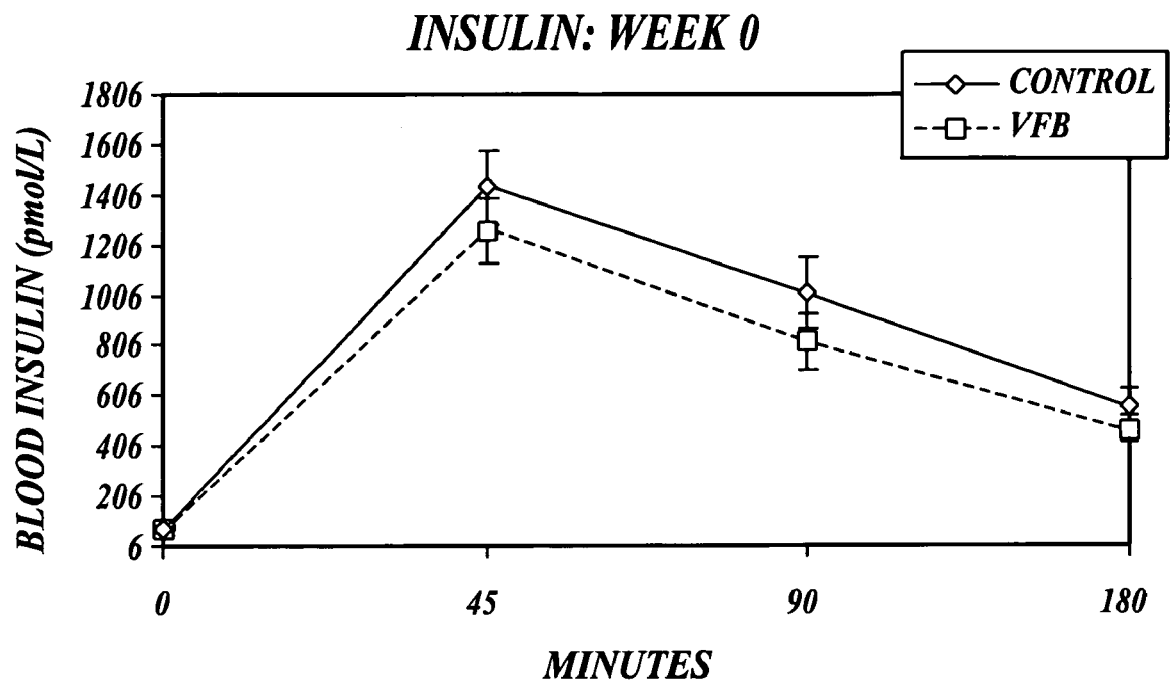
FIG. 3C graphically illustrates the postprandial insulin response in subjects provided with control and test breakfasts as measured at the beginning of the study, as described in EXAMPLE 2.
Figure 3D:
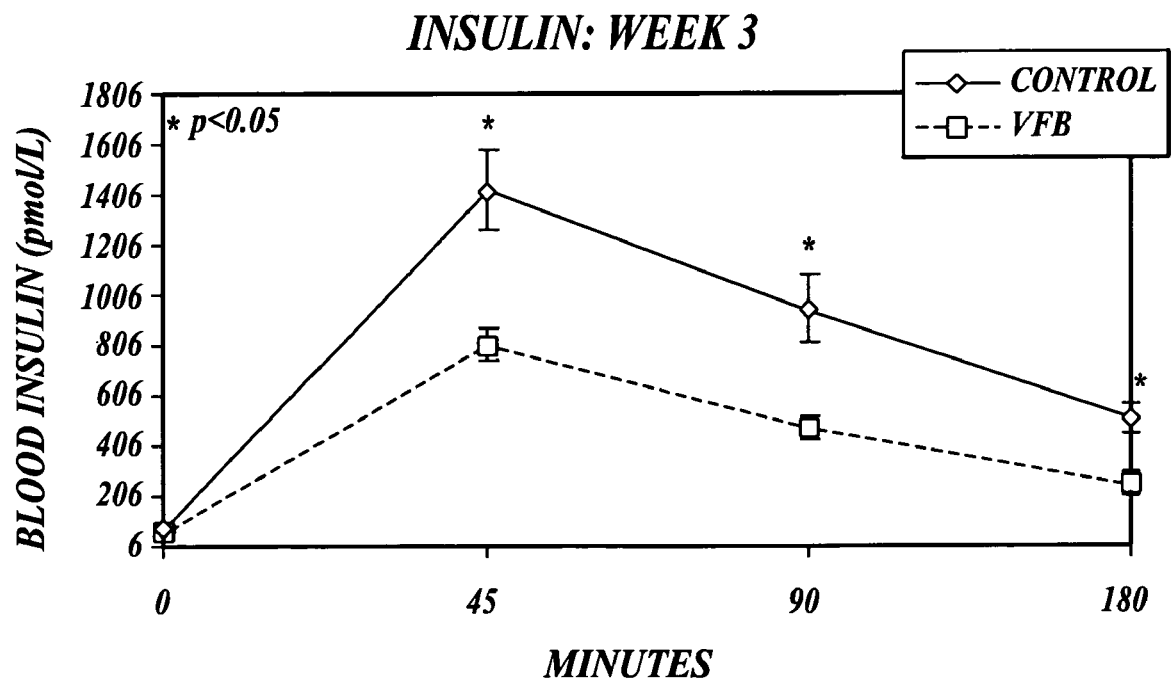
FIG. 3D graphically illustrates the postprandial insulin response in subjects provided with control and test breakfasts as measured during the third week of the study, as described in EXAMPLE 2.

5. Insulin: FIGS. 3C-D and Table 17 show a comparison of the postprandial insulin response in subjects provided with control and test VFB breakfasts. Subjects were given either the control breakfast or the test breakfast everyday for three weeks. Their blood insulin response was measured at the beginning of the study (week 0) and at the end of the study (week 3). All data points are means±SD. Significant differences at p<0.05 are indicated by an asterisk.

Figure 5:
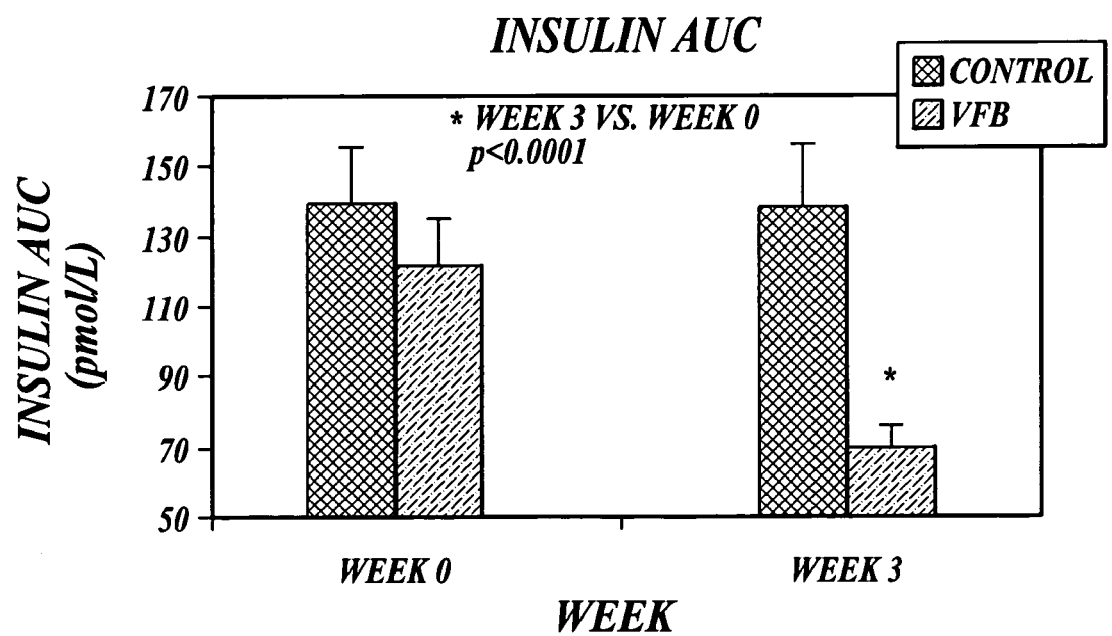
FIG. 5 shows the area under the curves for postprandial insulin responses at week 0 and week 3 for control and VFB, as described in EXAMPLE 2. All data points are means±SD. Significant differences at p<0.05 are indicated by an asterisk.

FIG. 5 shows the area under the curve (AUC) for postprandial insulin response at week 0 and week 3 for control and VFB. All data points are means±SD. Significant differences at p<0.05 are indicated by an asterisk.

TABLE 17

Comparison of Insulin Levels in Subjects Provided with Control and Test Breakfasts

| | Blood Insulin (pmol/L) | | | | |
|---|---|---|---|---|---|
| | 0 min | 45 min | 90 min | 180 min | AUC |
| | Week 0: Control | | | | |
| MEAN | 78.58 | 1436.58 | 1015.08 | 567.50 | 139.68 |
| SEM | 5.32 | 149.03 | 142.08 | 61.65 | 16.05 |
| | Week 0: VFB Treatment | | | | |
| MEAN | 80.67 | 1263.25 | 820.00 | 472.92 | 121.61 |
| SEM | 5.91 | 126.49 | 110.81 | 48.37 | 13.94 |
| | Week 3: Control | | | | |
| MEAN | 78.33 | 1420.42 | 949.75 | 515.25 | 138.81 |
| SEM | 7.85 | 161.39 | 137.58 | 58.68 | 17.60 |
| | Week 3: Control | | | | |
| MEAN | 70.00 | 808.75 | 479.75 | 256.25 | 69.46 |
| SEM | 6.25 | 65.72 | 44.71 | 46.63 | 6.85 |

Figure 6:
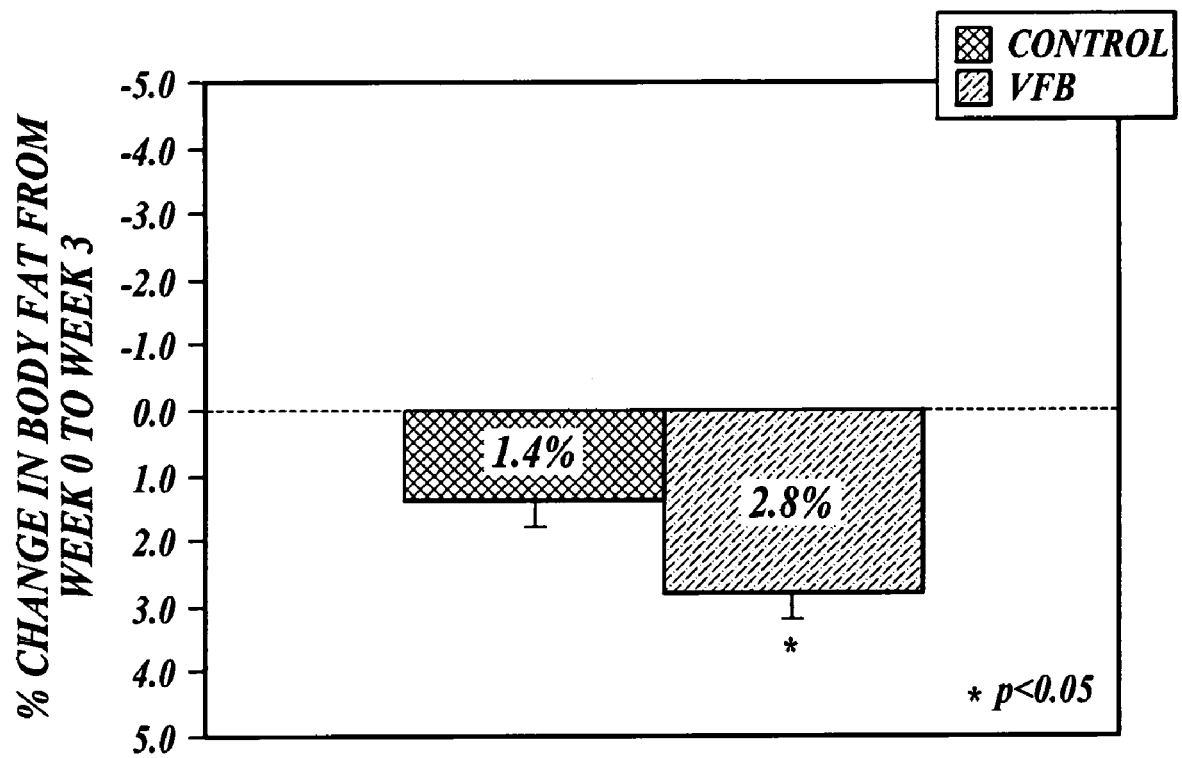
FIG. 6 graphically illustrates the change in percent body fat in subjects that consumed a test breakfast in comparison to subjects that consumed a control breakfast over a three week period, as described in EXAMPLE 2.

6. Percent Body Fat: An infrared interactance Futrex-5000® system (Futrex Inc, Gaithersburg, Md.) was used to assess body composition. FIG. 6 and Table 18 illustrate the change in percent body fat from week 0 to week 3 during the control in which participants consumed the control breakfast compared to the period in which participants consumed the test breakfast. Data are represented as means. Significant differences at p<0.05 are indicated by an asterisk.

TABLE 18

Change in Percent Body Fat in Subjects Provided Control or Test (VFB) Breakfasts

| Breakfast | Change in Percent Body Fat From Week 0 to Week 3 | |
|---|---|---|
| | MEAN | SEM |
| Control | −1.4 | 0.7 |
| VFB treatment | −2.8* | 0.4 |

Conclusions

Areas under the curves for glycemia (−23.13.5% vs. 0.42.3%, P=0.000022) and insulinemia (−40.54.5% vs. 2.02.9%, p=0.000012) were significantly reduced with VFB, compared to control. These decreases translated into a significant increase in insulin sensitivity after consumption of VFB compared to control (55.99.2% vs. 9.74.5%, P=0.00056). In addition, body fat was reduced by 2.8% from baseline following the 3 week period with VFB, compared to the control group, which experienced 1.4% body fat reduction (p<0.05). We concluded that prolonged consumption of VFB reduces body fat in individuals with impaired insulin sensitivity in the metabolic syndrome. A possible explanation includes an improvement in insulin sensitivity.

EXAMPLE 3

This Example provides an exemplary embodiment of a meal replacement product comprising a dietary fiber composition of the invention.

An exemplary dietary fiber blend (VFB) was made by combining glucomannan (greater than 80% pure from Konjac root), Xanthan gum (commercially sourced extracellular heteropolysaccharide from *Xanthomonas* bacteria), and alginate (commercially sourced medium viscosity sodium alginate from *Ascophyllum nodosum*). The composition of an exemplary dietary fiber blend (VFB) is shown in Table 19.

TABLE 19

VFB Fiber Blend Composition

| Ingredient | Amount |
|---|---|
| Glucomannan | 3500 mg (70%) |
| Xanthan Gum | 850 mg (17%) |
| Alginate | 650 mg (13%) |
| Total | 5000 mg |

A meal replacement product was formulated with the VFB fiber blend as shown in Table 20.

TABLE 20

Meal Replacement Composition

| Ingredient | Amount |
|---|---|
| Whey protein | 44% |
| Fructose | 14% |
| VFB fiber blend | 9% |
| Xylitol | 8% |
| Flavor | 8% |
| Lecithin | 7% |
| Vitamins and Minerals | 6% |
| Medium chain triglycerides | 4% |

Table 21 shows the vitamin and mineral provided per serving of the meal replacement product (RE=retinol equivalent units, NE=niacin equivalent units, mcg=microgram, mg=milligram).

TABLE 21

Vitamin and Mineral Provided Per Serving

| Vitamin A | 630 | RE |
|---|---|---|
| Vitamin D | 2.5 | Mcg |
| Vitamin E | 4.4118 | Mg |
| Vitamin C | 20 | Mg |
| Thiamine | 750 | Mcg |
| Riboflavin | 800 | Mcg |
| Niacin | 12 | NE |
| Vitamin B6 | 750 | Mcg |
| Vitamin B12 | 0.75 | Mcg |
| Folacin | 120 | Mcg |
| Pantothenic acid | 2.5 | Mg |
| Biotin | 75 | Mcg |
| Calcium | 400.5736 | Mg |
| Phosphorus | 250 | Mg |
| Iron | 2.77324 | Mg |
| Iodide | 40 | Mcg |
| Magnesium | 120 | Mg |
| Copper | 0.5 | Mg |
| Zinc | 6 | Mg |
| Potassium | 399.6344 | Mg |
| Sodium | 354.3036 | Mg |
| Manganese | 1 | Mg |
| Selenium | 20 | Mcg |
| Chromium | 20 | Mcg |
| Molybdenum | 25 | Mcg |

The flavor of the meal replacement can include, but is not limited to, any of the following: chocolate, strawberry, vanilla, pineapple, mango, peach, orange, mocha, and cherry. This meal replacement is a powder form. Each serving is 57 grams, to be mixed with a glass of water. One serving is taken at breakfast and at lunch in place of a regular meal.

EXAMPLE 4

This Example illustrates the effects on volunteers of consuming a meal replacement product comprising the dietary fiber composition (VFB) of the invention.

A middle-aged male volunteer took the meal replacement product described in EXAMPLE 3 twice a day for a 9-month trial. At the start of the trial, the volunteer weighed 247.2 pounds, had a BMI of 36, a waist measurement of 45.25 inches, a hip measurement of 47.25 inches, and a body fat measurement of 27.7%. At the end of the 9-month trial, the volunteer weighed 223.75 pounds, has a waist measurement of 43 inches, a hip measurement of 45.5 inches, and a body fat measurement of 25.7%. The volunteer complained of stomachache, loose stools, and hunger in the evening when he did not take the meal replacement.

A middle-aged female volunteer took the meal replacement product described in EXAMPLE 3 twice a day for a 9-month trial. At the start of the trial, the volunteer weighed 170 pounds, had a BMI of 30.3, a waist measurement of 36.5 inches, a hip measurement of 43 inches, and a body fat measurement of 46.6%. At the end of the 9-month trial, the volunteer weighed 156 pounds, had a waist measurement of 33.5 inches, and a hip measurement of 41 inches. The volunteer complained of diarrhea during the first 2 days of the trial and found herself drinking more water due to thirst.

A middle-aged female volunteer took the meal replacement product described in EXAMPLE 3 twice a day for a 9-month trial. At the start of the trial, the volunteer weighed 162.5 pounds, had a BMI of 27.9, a waist measurement of 37 inches, a hip measurement of 43 inches, and a body fat measurement of 41.9%. At the end of the 9-month trial, the volunteer weighed 141 pounds, had a waist measurement of 34 inches, a hip measurement of 41 inches, and a body fat measurement of 35.3%. The volunteer complained of minor headache during the first two weeks of the trial.

A middle-aged female volunteer took the meal replacement product described in EXAMPLE 3 twice a day for a 9-month trial. At the start of the trial, the volunteer weighed 172 pounds, had a BMI of 27.7, a waist measurement of 35.75 inches, a hip measurement of 43 inches, and a body fat measurement of 41.6%. At the end of the 9-month trial, the volunteer weighed 143 pounds, had a waist measurement of 31 inches, and a hip measurement of 38.25 inches. The volunteer found the diet plan reasonable and flexible.

EXAMPLE 5

This Example provides an exemplary embodiment of a dietary fiber composition (VFB) of the invention formulated as gelatin capsules.

An exemplary dietary fiber composition was formulated as 2 piece hard-gelatin capsules, with each capsule containing 500 mg of the composition shown in Table 22.

TABLE 22

VFB Capsule Composition

| Ingredient | Amount |
| --- | --- |
| Glucomannan | 350 mg (47.62%) |
| Xanthan Gum | 85 mg (11.56%) |
| Alginate | 65 mg (8.84%) |
| Rice Flour | 228 mg (31.02%) |
| Magnesium Stearate | 7 mg (0.95%) |
| Total | 735 mg |

EXAMPLE 6

This Example provides an exemplary embodiment of a dietary fiber composition of the invention formulated as an appetite control powder.

An exemplary dietary fiber composition was formulated as an appetite control power. Each bottle contains 182 g, which represents 26 servings. The contents per serving of the appetite control powder are shown in Table 23.

TABLE 23

Contents per Serving of SlimStyles Appetite Control Powder

| Ingredient | Amount |
| --- | --- |
| Glucomannan | 3.5 mg (50%) |
| Xanthan Gum | 0.65002 mg (9.29%) |
| Alginate | 0.85001 mg (12.14%) |
| Xylitol | 0.72898 mg (10.41%) |
| Lecithin | 0.04998 mg (0.71%) |
| Medium Chain Triglycerides | 0.04998 mg (0.71%) |

TABLE 23-continued

Contents per Serving of SlimStyles Appetite Control Powder

| Ingredient | Amount |
| --- | --- |
| Natural Orange Juice Flavor | 0.72002 mg (10.29%) |
| Orange Flavor | 0.36001 mg (5.14%) |
| Stevia Powder | 0.07497 mg (1.07%) |
| Syloid Silica | 0.01603 mg (0.12%) |
| Total | 7 mg |

EXAMPLE 7

This Example provides an exemplary embodiment of a dietary fiber composition (VFB) of the invention formulated as a meal replacement smoothie.

An exemplary dietary fiber composition was formulated as a meal replacement smoothie. The contents per serving of the meal replacement smoothie are shown in Table 24.

TABLE 24

Contents per Serving of SlimStyles Meal Replacement Smoothie

| Ingredient | Amount |
| --- | --- |
| Whey protein | 24.5 g (42.87%) |
| Ca (from Ca citrate) | 77 mg (0.67%) |
| Total Ca | 400.5736 mg |
| Mg (from Mg citrate) | 120 mg (1.38%) |
| Iron (from Fe fumarate) | 2.5 mg (0.01%) |
| Zn (from Zn citrate) | 6 mg (0.03%) |
| Se (rice chelate) | 20 mcg (0.01%) |
| Cr (from Cr chelate) | 20 mcg (0.00%) |
| Cu (from Cu chelate) | 0.5 mg (0.01%) |
| Mo (from Mo citrate) | 25 mcg (0.01%) |
| Mn (from Mn citrate) | 1 mg (0.01%) |
| Potassium citrate | 20 mg (0.10%) |
| I (KI) | 40 mcg (0.00%) |
| P (Calcium phosphate dehydrate) | 250 mg (2.63%) |
| Na (sodium chloride) | 55 mg (0.24%) |
| Beta Carotene | 6300 iu (0.04%) |
| Vitamin D2 | 100 iu (0.00%) |
| Vitamin E (acetate) | 6 iu (0.01%) |
| B1 thiamin HCl | 0.75 mg (0.00%) |
| B2 riboflavin | 0.8 mg (0.00%) |
| B3 niacinamide | 12 mg (0.02%) |
| Pantothenic acid (Ca Panto) | 2.5 mg (0.01%) |
| Folic Acid | 0.12 mg (0.00%) |
| B6 pyridoxine HCl | 0.75 mg (0.00%) |
| B12 cyanocobalamin | 0.5 mcg (0.00%) |
| Biotin | 75 mcg (0.01%) |
| Vitamin C | 20 mg (0.04%) |
| Glucomannan | 3.5 g (6.12%) |
| Xanthan Gum | 0.65 g (1.14%) |
| Sodium Alginate | 0.85 g (1.5%) |
| Stevia | 150 mg (0.26%) |
| Fructose | 7 g (12.25%) |
| Xylitol | 0.72898 mg (10.41%) |
| Chocolate Flavor | 1.3 g (2.27%) |
| Cocoa | 1 g (1.75%) |
| Coffee (Rich blend) | 2.3 g (4.02%) |
| Cream Flavor | 1.1 g (1.92%) |
| Lecithin | 4.4 g (7.70%) |
| Medium Chain Triglycerides | 2.4 g (4.20%) |
| Total | (100%) |

EXAMPLE 8

This Example describes a comparison of the viscosity profile of an exemplary fiber blend (VFB) to other fiber blends under various conditions.

Methods: A formulation of viscous fiber blend (VFB) was created which included 70% glucomannan (konjac), 13% xanthan and 17% alginate, as described in EXAMPLE 1. The VFB was compared with a konjac/xanthan (70:30) fiber blend and a konjac/alginate (70:30) fiber blend in distilled water, gastric conditions and intestinal conditions as follows.

Compositions tested:
(1) VFB: konjac (70%)/xanthan (13%)/alginate (17%)
(2) KX: konjac (70%)/xanthan (30%)
(3) KA: Konjac (70%)/alginate (30%)

Viscosity Profile Experiments: 5 g of test material was mixed with 350 g of fluid (either distilled water, gastric, or intestinal juice). The sample was blended for 30 seconds on low speed 2 on a Proctor/Silex blender. Viscosity readings were taken at 5, 10, 15, 20, 30, 45, 60, and 120 minutes. Gastric and intestinal fluids were prepared according to Universal Sample Preparation (USP) methodology.

Figure 9:
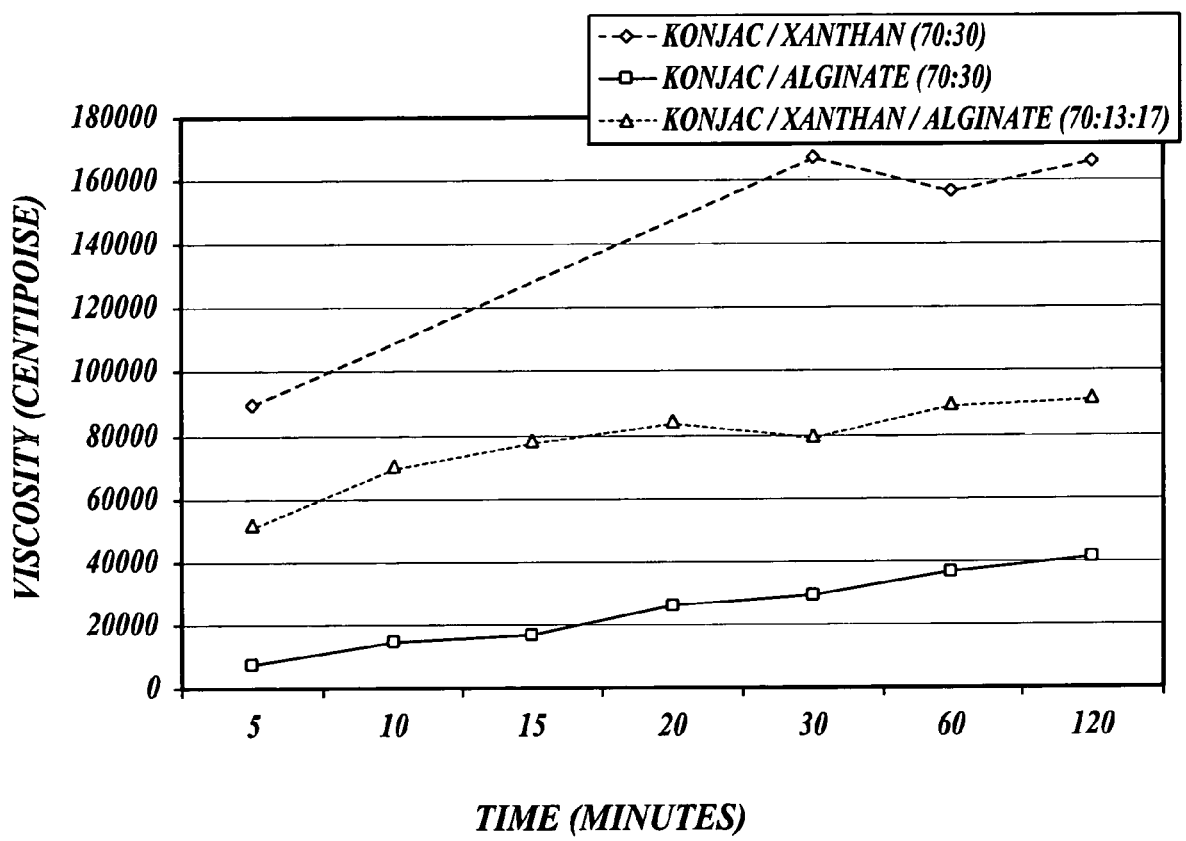
FIG. 9 graphically illustrates the viscosity profile of various fiber blends over time under intestinal conditions, as described in EXAMPLE 8.

Results:

Table 25 and FIG. 7 compare the viscosity profile of VFB compared with KX and KA under normal conditions (distilled water). Table 26 and FIG. 8 compare the viscosity profile of VFB compared with KX and KA under gastric conditions. Table 27 and FIG. 9 compare the viscosity profile of VFB compared with KX and KA under intestinal conditions. As shown in FIGS. 7, 8 and 9, the KA (konjac/alginate 70:30) fiber blend consistently has the lowest viscosity of the three fiber blends tested. Under neutral and gastric conditions the KX (konjac/xanthan 70:30) reaches maximum viscosity quickly (e.g., within about 15-20 minutes). The VFB blend (konjac (70%)/xanthan (13%)/alginate (17%)) starts at about the same viscosity as KA under neutral conditions, increases in viscosity over time under both gastric and intestinal conditions, and eventually reaches a greater viscosity than KX under neutral and gastric conditions. This combination also produces unexpectedly high viscosity values after 10 minutes when blended with gastric juice. Therefore, the addition of alginate to the KX combination unexpectedly provides a decrease in viscosity of VFB at neutral conditions, and results in a greater viscosity than KX alone over time.

TABLE 25

Viscosity Profile Comparison of VFB and Various Fiber Blends in Distilled Water

| Fiber blend | 5 min | 10 min | 15 min | 20 min | 30 min | 60 min | 120 min | avg temp | pH |
|---|---|---|---|---|---|---|---|---|---|
| KX: konjac/xanthan (70:30) | 53380 | 49080 | 47870 | 43950 | 49810 | 49251 | 47440 | 20.2 | 6.05 |
| KA: konjac/alginate (70:30) | 3960 | 11470 | 16730 | 18420 | 25940 | 43530 | 78850 | 20.2 | 6.35 |
| VFB (konjac/xanthan/alginate (70:13:17) | 4230 | 9230 | 16700 | 34970 | 43170 | 46010 | 90000 | 20.8 | 6.17 |

TABLE 26

Viscosity Profile Comparison of VFB and Various Fiber Blends Under Gastric Conditions

| Fiber blend | 5 min | 10 min | 15 min | 20 min | 30 min | 60 min | 120 min | avg temp | pH |
|---|---|---|---|---|---|---|---|---|---|
| KY: konjac/xanthan (70:30) | 35500 | 48020 | 70150 | 75400 | 78720 | 83290 | 87680 | 20.3 | 1.46 |
| KA: konjac/alginate (70:30) | 3210 | 11820 | 17664 | 18820 | 23580 | 29130 | 43460 | 20.2 | 3.85 |
| VFB (konjac/xanthan/alginate (70:13:17) | 44880 | 90000 | 116500 | 123600 | 135200 | 139600 | 249000 | 20.5 | 3.69 |

TABLE 27

Viscosity Profile Comparison of VFB and Various Fiber Blends Under Intestinal Conditions

| Fiber blend | 5 min | 10 min | 15 min | 20 min | 30 min | 60 min | 120 min | avg temp | pH |
|---|---|---|---|---|---|---|---|---|---|
| KX: konjac/xanthan (70:30) | 90000 | nd | nd | nd | 167500 | 156800 | 166200 | 20.2 | 7.88 |
| KA: konjac/alginate (70:30) | 6990 | 14470 | 16350 | 26030 | 29110 | 36600 | 40900 | 20.1 | 7.89 |
| VFB (konjac/xanthan/alginate (70:13:17) | 51490 | 70180 | 78640 | 84100 | 79480 | 90000 | 91900 | 20.5 | 7.92 |

The invention claimed is:

1. A granulated dietary fiber composition comprising granules, wherein each granule comprises from about 60% to about 80% (w/w) glucomannan, from about 10% to about 20% (w/w) xanthan gum, and from about 5% to about 20% (w/w) alginate.

2. The granulated dietary fiber composition of claim 1, wherein the dietary fiber composition produces at least a threefold increase in the viscosity of a solution simulating gastric conditions within 30 minutes after addition of the composition to a 70-fold (w/w) excess of the solution simulating gastric conditions having a pH of about 1.2 as compared to the initial viscosity of a solution comprising the composition under neutral conditions as measured in a 100-fold (w/w) excess of water.

3. The granulated dietary fiber composition of claim 1, wherein the dietary fiber composition produces at least a threefold increase in the viscosity of a solution simulating intestinal conditions within 30 minutes after addition of the composition to a 70-fold (w/w) excess of the solution simulating intestinal conditions having a pH between about 7.5 and about 8.0 as compared to the initial viscosity of a solution comprising the composition under neutral conditions as measured in a 100-fold (w/w) excess of water.

4. The granulated dietary fiber composition of claim 1, wherein each granule comprises from about 70% to about 80% (w/w) glucomannan, from about 10% to about 20% (w/w) xanthan gum, and from about 10% to about 20% (w/w) alginate.

5. The granulated dietary fiber composition of claim 1, wherein each granule comprises about 70% to about 80% (w/w) glucomannan, from about 10% to about 20% (w/w) xanthan gum, and from about 13% to about 17% (w/w) alginate.

6. The granulated dietary fiber composition of claim 5, wherein each granule comprises about 70% (w/w) glucomannan, about 13% (w/w) xanthan gum, and about 17% (w/w) alginate.

7. The granulated dietary fiber composition of claim 5, wherein each granule comprises about 70% glucomannan, about 17% (w/w) xanthan and about 13% (w/w) alginate.

8. The granulated dietary fiber composition of claim 1, wherein the composition comprises granules of from about 30 mesh to about 60 mesh.

9. The granulated dietary fiber composition of claim 8, wherein the composition comprises a combination of granules selected from the group consisting of 30 mesh, 40 mesh and 60 mesh granules.

10. The composition of claim 1, wherein the alginate is a medium viscosity alginate.

11. A method for preparing a granulated dietary fiber composition comprising the steps of:
(a) mixing from about 60% to about 80% (w/w) glucomannan, from about 10% to about 20% (w/w) xanthan gum, and from about 5% to about 20% (w/w) alginate;
(b) adding from about 30% to about 60% (w/w) water to the mixture of step (a);
(c) granulating to produce wet granules; and
(d) drying to produce a granulated dietary fiber composition.

12. The method of claim 11, further comprising selecting granules having a granule size ranging from about 30 mesh to about 60 mesh.

13. A granulated dietary fiber composition comprising granules produced by the method of claim 12.

14. The method of claim 11, wherein step (a) comprises mixing from about 70% to about 80% (w/w) glucomannan, from about 10% to about 20% (w/w) xanthan gum, and from about 5% to about 20% (w/w) alginate.

15. The method of claim 11, wherein step (a) comprises mixing from about 70% to about 80% (w/w) glucomannan, from about 10% to about 20% (w/w) xanthan gum, and from about 10% to about 20% (w/w) alginate.

16. The method of claim 11, wherein the granulating at step (c) is accomplished by at least one of agitation in mixing equipment: compaction, extrusion, or globulation.

17. The method of claim 11, wherein the drying at step (d) is accomplished by use of at least one of a fluid-bed dryer, an oven, or vacuum drying.

18. A granulated dietary fiber composition comprising granules produced by the method of claim 11.

19. The method of claim 11, wherein the alginate is a medium viscosity alginate.

20. A method for promoting satiety, promoting weight loss, lowering blood glucose levels, or lowering blood cholesterol levels in a mammal, comprising administering to a mammal an amount of a granulated dietary fiber composition effective to promote satiety, to promote weight loss, to lower blood glucose levels, or to lower blood cholesterol levels in the mammal, wherein the granulated dietary fiber composition comprises granules, wherein each granule comprises from about 60% to about 80% (w/w) glucomannan, from about 10% to about 20% (w/w) xanthan gum, and from about 5% to about 20% (w/w) alginate.

21. The method of claim 20, wherein each granule comprises from about 60% to about 80% (w/w) glucomannan, from about 10% to about 20% (w/w) xanthan gum, and from about 9% to about 17% (w/w) alginate.

22. The method of claim 20, wherein each granule comprises from about 70% to about 80% (w/w) glucomannan, from about 10% to about 20% (w/w) xanthan gum, and from about 5% to about 20% (w/w) alginate.

23. The method of claim 20, wherein each granule comprises from about 70% to about 80% (w/w) glucomannan, from about 10% to about 20% (w/w) xanthan gum, and about 9% to about 17% (w/w) alginate.

24. The method of claim 23, wherein each granule comprises about 70% glucomannan, about 13% xanthan and about 17% alginate.

25. The method of claim 23, wherein each granule comprises about 70% glucomannan, about 17% xanthan and about 13% alginate.

26. The method of claim 20, wherein the composition is administered to the mammal in an amount effective to promote weight loss.

27. The method of claim 20, wherein the alginate is a medium viscosity alginate.

UNITED STATES PATENT AND TRADEMARK OFFICE
CERTIFICATE OF CORRECTION

PATENT NO. : 8,062,686 B2
APPLICATION NO. : 11/400768
DATED : November 22, 2011
INVENTOR(S) : R. Gahler et al.

It is certified that error appears in the above-identified patent and that said Letters Patent is hereby corrected as shown below:

COLUMN     LINE

(56)     Refs.Cited     "Double-Blind Tria," should read
         (Other Publs.,     --Double-Blind Trial,--
Title Pg. 2, col. 1

In the Specification 2     11     "glucomanhan" should read
              --glucomannan--

18     56     "Week 3: Control" should read
              --Week 3: VFB Treatment--

24     46     "KY" should read --KX--

Signed and Sealed this
Fifth Day of November, 2013

Teresa Stanek Rea
*Deputy Director of the United States Patent and Trademark Office*